(12) United States Patent
Yoo

(10) Patent No.: US 7,772,220 B2
(45) Date of Patent: *Aug. 10, 2010

(54) METHODS AND COMPOSITIONS FOR REDUCING TOXICITY OF A PHARMACEUTICAL COMPOUND

(76) Inventor: Seo Hong Yoo, 537 Spencer Dr., Wyckoff, NJ (US) 07481

( * ) Notice: Subject to any disclaimer, the term of this patent is extended or adjusted under 35 U.S.C. 154(b) by 0 days.

This patent is subject to a terminal disclaimer.

(21) Appl. No.: 11/251,137

(22) Filed: Oct. 14, 2005

(65) Prior Publication Data

US 2006/0089331 A1    Apr. 27, 2006

Related U.S. Application Data

(60) Provisional application No. 60/619,199, filed on Oct. 15, 2004.

(51) Int. Cl.
*A61K 31/575* (2006.01)
*C07J 9/00* (2006.01)
*C07J 41/00* (2006.01)

(52) U.S. Cl. .................. 514/171; 514/182; 552/549; 552/550

(58) Field of Classification Search .............. None
See application file for complete search history.

(56) References Cited

U.S. PATENT DOCUMENTS

| | | | | |
|---|---|---|---|---|
| 3,845,770 A | 11/1974 | Theeuwes et al. | ........... | 128/260 |
| 3,916,899 A | 11/1975 | Theeuwes et al. | ........... | 128/260 |
| 4,036,954 A | 7/1977 | Murakami et al. | .......... | 424/176 |
| 4,092,428 A | 5/1978 | Murakami et al. | .......... | 424/317 |
| 4,113,882 A | 9/1978 | Okazaki et al. | ............. | 424/317 |
| 4,320,146 A | 3/1982 | Walser | ....................... | 424/319 |
| 4,327,725 A | 5/1982 | Cortese et al. | .............. | 128/260 |
| 4,585,790 A | 4/1986 | Padfield et al. | .............. | 514/471 |
| 4,681,876 A | 7/1987 | Marples et al. | ............. | 514/182 |
| 4,879,303 A | 11/1989 | Davison et al. | ............ | 514/356 |
| 5,057,321 A | 10/1991 | Edgren et al. | ............... | 424/413 |
| 5,149,537 A | 9/1992 | Azria et al. | .................. | 424/436 |
| 5,157,022 A | 10/1992 | Barbul | ......................... | 514/18 |
| 5,260,074 A | 11/1993 | Sipos | ......................... | 424/467 |
| 5,292,534 A | 3/1994 | Valentine et al. | ............ | 424/451 |
| 5,300,300 A | 4/1994 | Egidio et al. | ................ | 424/456 |
| 5,302,398 A | 4/1994 | Egidio et al. | ................ | 424/474 |
| 5,302,400 A | 4/1994 | Sipos | ........................ | 424/494 |
| 5,310,560 A | 5/1994 | Widauer | ..................... | 424/451 |
| 5,324,514 A | 6/1994 | Sipos | ....................... | 424/94.63 |
| 5,342,625 A | 8/1994 | Hauer et al. | ................ | 424/455 |
| 5,380,533 A | 1/1995 | Egidio et al. | ............... | 424/456 |
| 5,446,026 A | 8/1995 | Ruff et al. | ...................... | 514/15 |
| 5,470,581 A | 11/1995 | Grillo et al. | ................. | 424/479 |
| 5,484,776 A | 1/1996 | Racz et al. | .................... | 514/54 |
| 5,516,523 A | 5/1996 | Heiber et al. | ............... | 424/435 |
| 5,534,505 A | 7/1996 | Widauer | ..................... | 514/169 |
| 5,578,304 A | 11/1996 | Sipos | ........................ | 424/94.1 |
| 5,599,926 A | 2/1997 | Still et al. | .................... | 540/456 |
| 5,641,767 A | 6/1997 | Wess et al. | .................... | 514/172 |
| 5,653,987 A | 8/1997 | Modi et al. | ................. | 424/400 |
| 5,686,588 A | 11/1997 | Yoo | .......................... | 536/13.3 |
| 5,750,104 A | 5/1998 | Sipos | ....................... | 424/94.21 |
| 5,750,707 A | 5/1998 | Spargo | ....................... | 546/321 |
| 5,843,929 A | 12/1998 | Larson et al. | ............... | 514/182 |
| 5,846,964 A | 12/1998 | Ozeki | ........................ | 514/182 |
| 5,858,998 A | 1/1999 | Leuschner | .................. | 514/171 |
| 5,863,550 A | 1/1999 | Maeda et al. | .............. | 424/423 |
| 5,898,028 A | 4/1999 | Jensen et al. | ................... | 514/4 |
| 5,945,411 A | 8/1999 | Larson et al. | ............... | 514/171 |
| 5,965,164 A | 10/1999 | Fuisz et al. | ................. | 424/489 |
| 5,977,070 A | 11/1999 | Piazza et al. | .................. | 514/12 |
| 6,099,859 A | 8/2000 | Cheng et al. | ................ | 424/464 |
| 6,210,699 B1 | 4/2001 | Acharya et al. | ............. | 424/435 |
| 6,245,753 B1 | 6/2001 | Byun et al. | ..................... | 514/56 |
| 6,251,428 B1 * | 6/2001 | Yoo | .......................... | 424/455 |
| 6,309,663 B1 * | 10/2001 | Patel et al. | ................... | 424/450 |
| 6,635,628 B2 * | 10/2003 | Bouscarel et al. | ........... | 514/171 |
| 7,034,006 B2 | 4/2006 | Yedgar et al. | ................. | 514/42 |
| 7,166,299 B2 * | 1/2007 | Yoo | .......................... | 424/455 |
| 7,303,768 B2 | 12/2007 | Yoo | .......................... | 424/528 |
| 2001/0046521 A1 | 11/2001 | Zasloff et al. | ............... | 424/649 |
| 2002/0031558 A1 * | 3/2002 | Yoo | .......................... | 424/653 |

(Continued)

FOREIGN PATENT DOCUMENTS

| | | |
|---|---|---|
| AU | 37358/99 | 12/1999 |
| CN | 1450914 | 10/2003 |
| EP | 0086705 | 2/1983 |
| EP | 0 312 052 A1 | 4/1989 |
| EP | 0 599 282 A1 | 6/1994 |

(Continued)

OTHER PUBLICATIONS

2006 Chemical Abstracts catalog, published 2006 by Chemical Abstracts Service, p. 52.*
Chemical Abstracts Registry entry 191595-91-2, "Bamet R2" copyright 2007 American Chemical Society.*
Chemical Abstracts Registry entry 64480-66-6 "Glycoursodeoxycholic acid" copyright 2007 American Chemical Societ.*

(Continued)

*Primary Examiner*—Eric S Olson
(74) *Attorney, Agent, or Firm*—Baker Botts L.L.P.

(57) ABSTRACT

The present disclosure is related to clear aqueous solutions of one or more bile acids and either an aqueous soluble starch conversion product or a non-starch polysaccharide. Solutions of the disclosure may be administered to a subject in conjunction with a pharmaceutical compound having one or more toxic effects. In some embodiments, solutions of the disclosure are administered to a mammal in conjunction with a pharmaceutical compound associated with a peripherial neurotoxicity (e.g., cisplatin and/or suramin) to reduce or eliminate the neuropathic effect(s).

24 Claims, 6 Drawing Sheets

U.S. PATENT DOCUMENTS

| | | | |
|---|---|---|---|
| 2002/0081361 A1 | 6/2002 | Towb et al. | 426/548 |
| 2003/0044413 A1 | 3/2003 | Steer et al. | 424/145.1 |
| 2005/0158408 A1 | 7/2005 | Yoo | 424/728 |
| 2006/0051319 A1* | 3/2006 | Yoo | 424/85.1 |
| 2006/0089331 A1 | 4/2006 | Yoo | 514/58 |
| 2006/0142241 A1* | 6/2006 | Yoo | 514/59 |
| 2006/0188530 A1* | 8/2006 | Yoo | 424/400 |
| 2007/0072828 A1* | 3/2007 | Yoo | 514/60 |
| 2008/0057133 A1* | 3/2008 | Yoo | 424/528 |

FOREIGN PATENT DOCUMENTS

| | | | |
|---|---|---|---|
| EP | 1255566 A2 | | 11/2002 |
| FR | 2710267 | | 3/1995 |
| JP | 55 022616 A | | 2/1980 |
| JP | 61171421 | | 2/1986 |
| JP | 62153220 | | 7/1987 |
| JP | 63104925 | | 5/1988 |
| JP | 63243031 | | 10/1988 |
| JP | 60 24991 A | | 2/1994 |
| JP | 6024991 | | 2/1994 |
| WO | WO 99/61481 | | 12/1999 |
| WO | 00/04875 A2 | | 2/2000 |
| WO | 0004875 | | 2/2000 |
| WO | WO00/10552 | * | 3/2000 |
| WO | 01/56547 A2 | | 8/2001 |
| WO | WO 2004/012686 | | 2/2004 |
| WO | 2004/043342 | | 5/2004 |
| WO | WO 2004/043342 A2 | | 5/2004 |
| WO | 2004/096123 | | 11/2004 |
| WO | 2006/026555 A2 | | 3/2006 |
| WO | 2006/050165 | | 5/2006 |
| WO | 2006/057637 A1 | | 6/2006 |

OTHER PUBLICATIONS

Chemical Abstracts Registry entry 265093-50-3, "Bamet UD2" copyright 2007 American Chemical Society.*

The American Heritage Dictionary, Second College Edition, published 1982 by Houghton Mifflin Company, p. 1213.*

Takeda et al., "Prevention of Irinotecan (CPT-11)-Induced Diarrhea by Oral Alkalization Combined With Control of Defecation in Cancer Patients" International Journal of Cancer (2001) vol. 92 pp. 269-275.*

Schuldes et al., "Reversal of multidrug resistance and increase in plasma membrane fluidity in CHO cells with R-verapamil and bile salts" European Journal of Cancer (2001) vol. 37 pp. 660-667.*

Mishra et al., "Bleomycin-Mediated Pulmonary Toxicity: Evidence for a p53-Mediated Response" Am. J. Respir. Cell. Mol. Biol. (2000) vol. 22 pp. 543-549.*

Dudley et al., "Attenuated p53 activation in tumor-associated stromal cells accompanies decreased sensitivity to etoposide and vincristine" British Journal of Cancer (2008) vol. 99, pp. 118-125.*

Sauna et al., "Disulfiram, an old drug with new potential therapeutic uses for human cancers and fungal infections" Mol. Biosyst. (2005) vol. 1, pp. 127-134.*

Yamaguchi et al., "Regulation of Bax Activation and Apoptotic Response to Microtubule-damaging Agents by p53 Transcription-dependent and -independent Pathways" Journal of Biological Chemistry (2004) vol. 279 No. 38, pp. 39431-39437.*

Howard et al., "Suramin Increases p53 Protein Levels but Does Not Activate the p53-dependent G1 Checkpoint Clinical Cancer Research (1996) vol. 2 pp. 269-276.*

Barbarotto et al., "Differential Effects of Chemotherapeutic Drugs Versus the MDM-2 Antagonist Nutlin-3 on Cell Cycle Progression and Induction of Apoptosis in SKW6.4 Lymphoblastoid B-Cells" Journal of Cellular Biochemistry (2008) vol. 140, pp. 595-605.*

Williams et al., "The Proteasome Inhibitor Bortezomib Stabilizes a Novel Active Form of p53 in Human LNCaP-Pro5 Prostate Cancer Cells" Cancer Research (2003) vol. 63 pp. 7338-7344.*

Fox et al., "Short Analytical Review: Mechanism of Action for Leflunomide in Rheumatoid Arthritis" Clinical Immunology (1999) vol. 93 No. 3, pp. 198-208.*

Youlyouz et al., "Identification of a novel p53-dependent activation pathway of STAT1 by antitumour genotoxic agents" Cell Death and Differentiation (2008) vol. 15 pp. 376-385.*

Hempfling et al., "Systematic review: ursodeoxycholic acid—adverse effects and drug interactions" Alimentary Pharmacology and Therapeutics (2003) vol. 18 pp. 963-972.*

Coudron et al., "In-vitro evaluation of nitrofurantoin as an alternative agent for metronidazole in combination antimicrobial therapy against Helicobacter pylori" Journal fo Antimicrobial Chemotherapy (1998) vol. 42 pp. 657-660.*

Lee et al., "Regulation of Cyclin-Dependent Kinase 5 and p53 py ERK1/2 Pathway in the DNA Damage-Induced Neuronal Death" Journal of Cellular Physiology (2007) vol. 210 pp. 784-797.*

Singhal et al., "Thalidomide in Cancer: Potential Uses and Limitations" BioDrugs (2001) vol. 15 No. 3, pp. 163-172.*

Cole et al., "Efficacy and Safet of Perhexiline Maleate in Refractory Angina" Circulation (1990) vol. 81 pp. 1260-1270.*

Govindarajan et al., "Irinotecan and thalidomide in metastatic colorectal cancer" Oncology (2000) vol. 14 No. 12 suppl 13, abstract.*

Graham et al., "Nitrofurantoin quadruple therapy for Helicobacter pylori infection: effect of metronidazole resistance" Alimentary Pharmacology and Therapeutics (2001) vol. 15 pp. 513-518.*

Itoh et al., "Antibacterial action of bile acids against Helicobacter pylori and changes in its ultrastructural morphology: effect of unconjugated dihydroxy bile acid" Journal of Gastroenterology (1999) vol. 34 pp. 571-576.*

Scheithauer et al., "Direct effects of the hypoxic cell sensitizer misonidazole on colony formation in a human tumor cloning assay" Cancer Drug Delivery (1986) vol. 3 No. 1, abstract.*

Jones et al., "The role of dexamethasone in the modification of misonidazole pharmacokinetics" British Journal of Cancer (1983) vol. 48 No. 4, pp. 553-557.*

"Dacarbazine", Aidsmap Treatment and Care, http://www.aidsmap.com/en/docs/9685F4D7-D57C-4F10-A41F-D5EDF7811B3A.asp , pp. 1, Feb. 6, 2006.

"Drug Information: Dacarbazine", Medline Plus, http://www.nlm.nih.gov/medlineplus/druginfo/medmaster/a682750.html , pp. 2, Apr. 1, 2003.

"Dacarbazine", NCI Terminology Browser, http://nciterms.nci.nih.gov/NCIBrowser/PrintableReport.jsp?dictionary=NCI_Thesaurus &code=C411 , pp .3, Nov. 2005.

P.J. Neveu, "The Effects of Thiol Moiety of Levamisole on Both Cellular and Humoral Immunity During the Early Response to a Hapten-Carrier Complex" Clin. Exp. Immunol. vol. 32, pp. 419-422, 1978.

E. Nagy et al., "Imuthiol Inhibits the Etoposide-Induced Apoptosis in HL-60 Cells" Immunology Letters vol. 64, pp. 1-4, 1998.

"An Assessment of the In Vivo Biological Effects of Diethyldithiocarbamate (DTC) in HIV-Infected Patients", ClinicalTrials.gov, http://www.clinicaltrials.gov/ct/show/NCT00000650; jsessionid=AF8903A542A345FA86641E2A559AC8-C9?order=1, pp. 6, Feb. 27, 2006.

Hubner et al., "Enhancement of Monocyte Antimycobacterial Activity by Diethyldithiocarbamate (DTC)" Int. J. Immunopharmac, vol. 13, pp. 1067-1072, 1991.

"Diethyldithiocarbamate", http://nciterms.nci.nih.gov/NCIBrowser/ConceptRecords.jsp?, pp. 2, Feb. 6, 2006.

"Proventil", PDR Health, http://www.pdrhealth.com/drug_info/rxdrugprofiles/drugs/pro1360.shtml, pp. 5, Feb. 8, 2006.

"Powered by Dorland's Illustrated Medical Dictionary: E", MerckSource, http://www.mercksource.com/pp/us/cns/cns_hl_dorlands.jspzQzpgzEzzSzppdocszSzuszSzcommonzSzdorlandsz SzdorlandzSzdmd_e_17zPzhtm, pp. 3, Feb. 27, 2006.

F. S. Giorgi et al., "The role of norepinephrine in epilepsy: from the bench to the bedside" Neurosci. Behavioral. Rev.. vol. 28, pp. 507-524, 2004.

K. Bodin et al., "Antiepileptic drugs increase plasma levels of 4beta-hydroxycholesterol in humans: evidence for involvement of cytochrome p450 3A4" J. Biol. Chem. vol. 276, pp. 38685-38689, Oct. 19, 2001.

V.S. Kasture et al.,"Anticonvulsant activity of Albizzia lebbeck leaves" Indian Journal of Experimental Biology vol. 34, pp. 78-80, Jan. 1996.

V.S. Kasture et al.,"Anticonvulsive activity of Albizzia lebbeck, Hibiscus rosa sinesis and Butea monosperma in experimental animals" Journal of Ethnopharmacology vol. 71, pp. 65-75, 2000.

P.P. But et al., "Ethnopharmacology of bear gall bladder: I" Journal of Ethnopharmacology vol. 47, pp. 27-31, 1995.

K.G. Rajesh et al., "Hydrophilic Bile Salt Ursodeoxycholic Acid Protects Myocardium Against Reperfusion Injury in a P13K/Akt Dependent Pathway", Journal of Molecular and Cellular Cardiology, vol. 39, pp. 766-776, 2005.

Cecilia M.P. Rodrigues et al., "Ursodeoxycholic Acid May Inhibit Deoxycholic Acid-Induced Apoptosis by Modulating Mitochondrial Transmembrane Potential and Reactive Oxygen Species Production", Molecular Medicine, vol. 4, pp. 165-178, 1998.

"Drug Information: Hydralazine", Medline Plus, http://www.nlm.nih.gov/medlineplus/druginfo/medmaster/a682246.html , pp. 3, Apr. 1, 2003.

"Drug Information: Isoxsuprine (Systemic)", Medline Plus, http://www.nlm.nih.gov/medlineplus/druginfo/uspdi/202310.html , pp. 4, Jul. 15, 1994.

"Drug Information: Nylidrin (Systemic)", Medline Plus, http://www.nlm.nih.gov/medlineplus/druginfo/uspdi/202416.html , pp. 3, May 14, 1993.

"Drug Information: Dyphylline (Systemic)", Medline Plus, http://www.nlm.nih.gov/medlineplus/druginfo/uspdi/202752.html , pp. 4, Jun. 14, 1999.

"Drug Information: Bronchodilators, Andrenergic (Inhalation)", Medline Plus, http://www.nlm.nih.gov/medlineplus/druginfo/uspdi/202095.html , pp. 12, Jun. 25, 2003.

"Colfosceril Palmitate", Tiscali, http://www.tiscali.co.uk/lifestyle/healthfitness/health_advice/netdoctor/archive/100003422.html , pp. 2, 1998-2004.

"Selenium", PDR Health, http://www.pdrhealth.com/drug_info/nmdrugprofiles/nutsupdrugs/sel_0232.shtml, pp. 8, Feb. 27, 2006.

"Clean, Beautiful, Healthy Life ", LG Household & Health Care, http://www.lgcare.com/english/aboutus/06.html, pp. 3, Feb. 27, 2006.

"Zovirax", PDRhealth, http://www.pdrhealth.com/drug info/rxdrugprofiles/drugs/zov1505.shtml , pp. 4, Feb. 8, 2006.

"Denavir", PDRhealth, http://www.pdrhealth.com/drug info/rxdrugprofiles/drugs/den1123.shtml , pp. 2, Feb. 8, 2006.

V. Fontes et al., "Recurrent Aphthous Stomatitis: Treatment With Colchicine. An Open Trial of 54 Cases", Ann. Dermatol. Venereol. vol. 129, pp. 1365-1369 , (with abstract) 2002.

"Drug Information: Celecoxib", Medline Plus, http://www.nlm.nih.gov/medlineplus/druginfo/medmaster/a699022.html , pp. 4, Jan. 1, 2006.

R.L. Wynn, "New Reports on Dental Analgesics. NSAIDs and Cardiovascular Effects, Celecoxib for Dental Pain, and a New Analgesic—Tramadol With Acetaminophen" General Dentistry vol. 50, pp. 218-220, 222, May 2002.

R.L. Wynn, "Update on Nonprescription Pain Relievers for Dental Pain", General Dentistry vol. 52, pp. 94-98 ,Mar. 2004.

P.M. Preshaw et al., "Self-medication for the control of dental pain: what are our patients taking?", Dent Update vol. 21, pp. 299-301, 304, Sep. 1994.

A.D. McNaught, "Nomenclature of Carbohydrates", Pure and Applied Chemistry, vol. 68, pp. 1919-2008, 1996.

D.L. Nelson, "Carbohydrates and Glycobiology", Lehninger Principles of Biochemistry,Fourth Edition, pp. 238-271, 2005.

H.R. Horton, "Carbohydrates", Principles of Biochemistry, Second edition, pp. 228-234, 1996.

Gerhard Schmid, "Preperation and Industrial Production of Cyclodextrins", Comprehensive Supramolecular Chemistry, vol. 3, pp. 41-56, 1996.

Frömming, "Cyclodextrins", Cyclodextrins in Pharmacy, Chapter 1, pp. 1-18, 1994.

Frömming, "Cyclodextrin Derivatives", Cyclodextrins in Pharmacy, Chapter 2, pp. 19-32, 1994.

Lehninger et al., "Carbohydrates and Glycobiology", Principles of Biochemistry, pp. 301-307, 2000.

D.S. Alberts et al., "Phase III Trial of Ursodeoxycholic Acid to Prevent Colorectal Adenoma Recurrence", Journal of National Cancer Institute, vol. 97, No. 11, pp. 846-853, Jun. 1, 2005.

D. Gaist et al.; "Statins and Risk of Polyneuropathy"; Neurology, vol. 58; pp. 1333-1337, May 2002.

D. Chapman-Shimshoni et al.; "Simvastatin Induces Apoptosis of B-CLL cells by Activation of Mitochondrial Caspase 9"; Experimental Hematology, vol. 31; pp. 779-783, 2003.

C.J. Newton et al.; "Fluvastin Induces Apoptosis of Vascular Endothelial Cells: Blockade by Glucocorticoids"; Cardiovascular Surgery, vol. 11, No. 1; pp. 52-60, 2003.

M.A. Vandelli et al.; "2-Hydroxypropyl-β-Cyclodextrin Complexation With Ursodeoxycholic Acid"; International Journal of Pharmaceutics, vol. 118; pp. 77-83, 1995.

J.F. Dasta et al.; "Comparison of Visual and Turbidimetric Methods for Determining ShortTerm Compatibility of Intravenous Critical-Care Drugs"; American Journal of Hospital Pharmacy; vol. 45; pp. 2361-2366, Nov. 1988.

C.A. Ventura et al.; "Improvement of Water Solubility and Dissolution Rate of Ursodeoxycholic Acid and Chenodeoxycholic Acid by Complexation With Natural and Modified β-Cyclodextrins"; International Journal of Pharmaceutics; vol. 149; pp. 1-13, 1997.

M. Föocking et al; "Statins Potentiate Caspase-3 Activity in Immortalized Murine Neurons"; Neuroscience Letters; vol. 355; pp. 41-44, 2003.

Michael B. Jacobs; "HMG-CoA Reductase Inhibitor Therapy and Peripheral Neuropathy"; www.PubMed.com ; pp. 3, Jun. 1, 1994.

Chad Silverberg; "Atorvastatin-Induced Polyneuropathy"; www.PubMed.com ; pp. 5, Nov. 4, 2003.

A.C. Peltier et al.; "Recent Advances in Drug-Induced Neuropathies"; Current Opinion in Neurology, vol. 15; pp. 633-638, 2002.

Park et al.; "Cisplatin-Induced Apoptotic Cell Death in Mouse Hybrid Neurons Is Blocked by Antioxidants Through Suppression of Cisplatin-Mediated Accumulation of p53 but Not of Fas/Fas Ligand"; Journal of Neurochemistry, vol. 75, No. 3; pp. 946-953, 2000.

R. Panini et al.; "Improvement of Ursodeoxycholic Acid Bioavailability by 2-Hydroxypropyl-β-Cyclodextrin Complexation in Healthy Volunteers"; Pharmacological Research; vol. 31, No. 314; pp. 205-209, 1995.

Kirk et al.; "Inclusion Compounds"; Encyclopedia of Chemical Technology, Fourth Edition; vol. 14; pp. 125-135, 1995.

PCT Notification of Transmittal of the International Search Report and Written Opinion PCT/US2006/008925, 10 pages, Mailing Date Jul. 21, 2006.

Cannon et al. "Reduction of pain on intravenous infusion with bile salt formulations for a macrolide antibiotic" International Journal of Pharmaceutics, vol. 114, No. 1 (pp. 65-74), Jul. 13, 1994.

Villaneuva et al. "Effect of Bile Acids of Hepatobiliary Transport of Cisplatin by Perfused Rat Liver" Pharmacology and Toxicology, vol. 80, No. 3 (pp. 111-117), Sep. 29, 1996.

Dominguez et al. "Low in Vivo Toxicity of a Novel Cisplatin-Ursodeoxycholic Derivative (Barnet-UD2) with Enhanced Cytostatic Activity versus Liver Tumors" Journal of Pharmacology and Experimental Therapeutics, vol. 297, No. 3 (pp. 1106-1112), Jan. 16, 2001.

International Search Report and Written Opinion for International Application No. PCT/US2005/037211 (16 pages), Feb. 13, 2007.

International Preliminary Report on Patentability for International Application No. PCT/US2005/037211 (10 pages), Apr. 26, 2007.

Notification Concerning Transmittal of International Preliminary Report on Patentability; PCT/US2006/008925; pp. 6, Apr. 16, 2008.

Communication pursuant to Article 94(3) EPC; Application No. 05 813 305.9-1216; pp. 7, Mar. 7, 2008.

CN Office Action; Application No. 200580028815.X; pp. 10, Mar. 13, 2009.

Isreali Office Action; Application No. 181434; pp. 12, Mar. 22, 2009.

CN Office Action; Application No. 200480044467.0; pp. 7, Mar. 27, 2009.
CN Office Action; Application No. 200580034884.1; pp. 6, Mar. 27, 2009.
Hofmann et al.; "Bile Acid Solubility and Preperation in Vitro and in Vivo: The Role of Conjugation, pH, and Ca2+ Ions"; Journal of Lipid Research, vol. 33; pp. 617-626, 1992.
Kimura et al.; "A Case of Cerebrotendinous Xanthomatosis: Effects of Ursodeoxycholic Acid Administration on Serum Bile Acids and Cholestanol"; Jap J Med, vol. 21, No. 3; pp. 210-215, Jul. 1982.
Ribatti et al.; "Development of the Blood-Brain Barrier: A Historical Point of View"; The Anotomical Record (Part B: New Anat.); pp. 6, 2006.
Ota et al.; "Metabolism of Bile Acids IV*. Absorption, Distribution, Excretion, and Metabolism of Orally Administered Ursodeoxycholic Acid in Rats"; Hiroshima Journal of Medical Sciences, vol. 26, No. 4; pp. 233-251, Dec. 1977.
MacWalter et al.; "A Benefit-Risk Assessment of Agents Used in the Secondary Prevention of Stroke"; Drug Safety; vol. 25, No. 13; pp. 943-963, 2002.
Wardlaw et al.; "Thrombolysis for Acute Ischaemic Stroke"; Cochrane Database of Systematic Views; Issue 3; pp. 98, 2003.
International Preliminary Report on Patentability; PCT/US2006/036325; pp. 8, Mar. 26, 2009.
Chinese Office Action; Application No. 200580037307.8; pp. 6, May 15, 2009.
European Office Action; Application No. 05 792 858.2-2123; pp. 4, May 20, 2009.
Higginbottom et al., International Journal of Pharmaceutics, vol. 109, pp. 173-180, 1994.
XP 002337365, Jul. 8, 1987, XP (abstract).
XP 002337364, Oct. 7, 1988, XP (abstract).
XP 002337367, Feb. 1, 1994, XP (abstract).
XP 002337363, May 10, 1998, XP (abstract).
H.P.R. Bootsma et al.; "β-Cyclodextrin as an Excipient in Solid Oral Dosage Forms: in Vitro and in Vivo Evaluation of Spray-Dried Diazepam-β-Cyclodextrin Products"; Inernation Journal of Pharmaceutics, vol. 51; pp. 213-223, 1989.
M.G. Allwood et al.; "Stability of Ampicillin Infusions in Unbuffered and Buffered Saline"; International Journal of Pharmaceutics, vol. 97; pp. 219-224, 1993.
PCT International Search Report PCT/US2004/039507 (12 pages), Mailing Date May 8, 2005.
PCT International Search Report and Written Opinion, PCT/US2004/039507, 29 pages, Mailing Date Oct. 25, 2005.
International Preliminary Report on Patentability and Written Opinion for International Application No. PCT/US2004/039507 (21 pages), Jun. 7, 2007.
Carey, MD et al. "Micelle Formation by Bile Salts Physical-Chemical and Thermodynamic Considerations" Arch. Intern. Med., vol. 130 (pp. 506-527), Oct. 1972.
Hirai et al. "Mechanisms for the Enhancement of the Nasal Absorption of Insulin by Surfactants" International J. of Pharmaceutics, vol. 9 (pp. 173-184), 1981.
Reynier et al. "Comparative Effects of Cholic, Chenodeoxycholic, and Ursodeoxycholic Acids on Micellar Solubilization and Intestinal Absorption of Cholesterol" J. of Lipid Research, vol. 22 (pp. 467-473), 1981.
Mollan, Jr. et al. "On of Aqueous Soluble Starch Conversion Products" Maltodextrin (pp. 308-349), 1995.
"Saccharide Composition Typical Carbohydrate Profiles" GPC Technical Bulletin TB30-021296, Grain Processing Corp. (1 page), 1999.
Nagamatsu "Phase I Clinical Study of Ursodesoxycholic Acid" Jpn. Pharmacol. Ther. vol. 22, No. 6 (pp. 145-159) 1997.
Hammad et al. "Solubility and Stability of Tetrazepam in Mixed Micelles" European J. of Pharmaceutical Sciences, vol. 7, (pp. 49-55) 1998.
Hammad et al. "Increasing Drug Solubility by Means of Bile Salt-Phosphatidylcholine-Based Mixed Micelles" European J. of Pharmaceutics and Biopharmaceutics, vol. 46 (pp. 361-367), 1998.
"Maltrin Maltodextrins & Corn Syrup Solids Chemical and Physical Properties" GPC Technical Bulletin, TB31-021296, Grain Processing Corp. (Brochure + 4 pages), 1999.

Verrips et al. "Effect of Simvastatin in Addition to Chenodeoxycholic Acid in Patients with Cerebrotendinous Xanthomatosis" Metabolism, vol. 48, No. 2 (pp. 233-238), Feb. 1999.
International Search Report and Written Opinion for International Application No. PCT/US2006/036325 (13 pages), Jun. 4, 2007.
Igimi et al. "ph-Solubility Relations of Chenodeoxycholic and Ursodeoxycholic Acids: Physical-Chemical Basis for Dissimilar Solution and Membrane Phenomena" J. of Lipid Research, vol. 21 (pp. 72-90), 1980.
Hollander et al. "Intestinal Absorption of Aspirin Influence of pH, Taurocholate, Ascorbate and Ethanol" J. of Lab. Clin. Med., vol. 98, No. 4 (pp. 591-595), Oct. 1980.
Itoh et al.; "Antibacterial action of bile acids against Helicobacteria pylori and changes inits ultrastructural morphology: effect of unconjugated dihydroxy bile acid"; J. Gastroenterol, vol. 34, pp. 571-576, 1999.
Knopp et al., "Long-Term Blood Cholesterol-Lowering Effects of a Dietary Fiber Supplement", Am J Pre. Med (1999) 17(1):18-23.
F. Lanzarotto et al., "Effect of Long-Term Simvastatin Administration as an Adjunct to Ursodeoxycholic Acid: Evidence for a Synergistic Effect on Biliary Bile Acid Composition but Not on Serum Lipids in Humans", GUT, (1999) vol. 4 pp. 552-556.
Leuschner et al., "Oral Budesonide and Ursodeoxycholic Acid for Treatment of Primary Biliary Cirrhosis: Results of a Prospective Double-Blind Trial", Gastroenterology, (1999) vol. 117 pp. 918-925.
Na et al., "Cloud Point of Nonionic Surfactants: Modulation with Pharmaceutical Excipients", Pharmaceutical Research, (1999) vol. 16, No. 4 pp. 562-568.
Osato et al., "Osmotic Effect of Honey on Growth and Viability of *Helicobacter pylori*", Digestive Diseases and Sciences, (1999) vol. 44, No. 3 pp. 462-464.
Invernizzi et al. "Differences in the Metabolism and Disposition of Ursodeoxycholic Acid and of its Taurine-Conjugated Species in Patients with Primary Biliary Cirrhosis" Hepatology, vol. 29, No. 2 (pp. 320-327), Feb. 1999.
Wacker Biochem. Corp., advertisement, C&EN, 31 (Apr. 12, 1999).
International Search Report and Written Opinion; PCT/US2005/039089; pp. 15, Mailed: May 24, 2006.
Notification Concerning Transmittal of International Preliminary Report on Patentability; PCT/US2006/008925; pp. 6, Apr. 16, 2008.
Binek et al., "Bedeutung von Ursodeoxycholsäure bei der Eradikation von *Helicobacter pyloni*", Schweitz Med Wochenschr (1996) 126 (Suppl. 79): 44S-46S.
Crosignani, et al., "Clinical Pharamcokinetics of Therapeutic Bile Acids", Clin. Pharmacokinet, (1996) vol. 30, No. 5 pp. 333-358.
Han et al., "The Interaction of pH, Bile and *Helicobacter pylori* May Explain Duofenial Ulcer", American Journal of Gastroenterology (1996) vol. 91, No. 6, pp. 1135-1137.
Mohler et al., "Effect of Ursodeoxycholic Acid on HCV Replication in Subtyped Chronic Hepatitis C", Digestive Diseases and Sciences, (1996) vol. 41, No. 6 p. 1276.
Newman et al., "Starch", Analytical Profiles of Drug Substances, (1996) Bristol-Myer Squibb Pharmaceutical Research Institute, New Brunswick, NJ, pp. 523-577.
Nishigaki, et al., "Ursodeoxycholic Acid Corrects Defective Natural Killer Activity by Inhibiting Prostaglandin $E_2$ Production in Primary Biliary Cirrhosis", Digestive Diseases and Sciences, (1996) vol. 41, No. 7, pp. 1487-1493.
Panini et al., "The Influence of 2-Hydroxypropyl-β-Cyclodextrin on the Haemolysis Induced by Bile Acids", J. Pharm. Pharmacol., (1996) vol. 48 pp. 641-644.
Tanaka et al., "Ligand-Independent Activiation of the Glucocorticord Receptor by Ursodeoxycholic Acid", The Journal of Immunology (1996) 156:1601-1608, 1996.
Buckley et al., "Controlled Release Drugs in Overdose Clinical Consideration", Drug Safety (1996) vol. 12, No. 1 pp. 73-84.
Keith D. Lindor, M.D., "Ursodiol for Primary Sclerosing Cholangitis", The New England Journal of Medicine, (1997) vol. 336, No. 10., pp. 691-695.
Oliva et al., "Ursodeoxycholate Alleviates Alcoholic Fatty Liver Damage in Rats", Alcohol Clin Exp Res., (1998), vol. 22, No. 7,pp. 1538-1543.

Sinisalo et al., "Ursodeoxycholic Acid and Endothelial-Dependent, Nitric Oxide-Independent Vasodilatation of Forearm Resistance Arteries in Patients with Coronary Heart Disease", Br. J. Clin. Pharamcol., (1999) vol. 47 pp. 661-665.

Angelin et al., "Effects of Ursodeoxycholic Acid on Plasma Lipids", Scand J. Gastroenterol. (1994) 29 Suppl 204:24-26.

I. Björkhem, "Inborn Errors of Metabolism with Consequences for Bile Acid Biosynthesis: A Minireview", Scand J. Gastroenteral (1994) 29 Suppl. 204:68-72.

A. Björkland and T.H. Totterman, "Is Primary Biliary Cirrhosis an Autoimmune Disease?", Scand J. Gastroenteral (1994) 29 Suppl. 204:32-9.

Jorgensen et al., "Characterisation of patients with a complete biochemical response to ursodeoxycholic acid", GUT (1995) 36:935-938, .

Kimura et al., "A 1-h Topical Therapy for the Treatment of *Helicobacter pylori* Infection", Am. J. Gastercenterol. (1995) vol. 90, No. 1, pp. 60-63.

Lindor et al., "The Combination of Ursodeoxycholic Acid and Methotrexate for Patients with Primary Biliary Cirrhosis: The Results of a Pilot Study", Hepatology (1995) vol. 22, No. 4 pp. 1158-1162.

Rodrigues et al., "The Site-Specific Delivery of Ursodeoxycholic Acid to the Rat Colon by Sulfate Conjugation", Gastroenterology (1995) vol. 109 pp. 1835-1844.

Simoni et al., "Bioavailability Study of a New, Sinking, Enteric-Coated Ursodeoxycholic Acid Formulation", Pharmacological Research (1995) vol. 31, No. 2 pp. 115-119.

P.J. Sinko, "Utility of Pharmacodynamic Measures for Assessing the Oral Bioavailability of Peptides. 1. Administration of Recombinant Salmon Calcitonin in Rats", Journal of Pharmaceutical Sciences, (1995) vol. 84, No. 11, pp. 1374-1378.

A. Benjamin Suttle and Kim L. R. Brouwer, "Regional Gastronintestinal Absorption of Ranitidine in the Rat", Pharmaceutical Research, (1995) Vol. 12, No. 9 pp. 1311-1315. 1995.

"Pharmaceutical Necessities", Remington: The Science and Practice of Pharmacy, Mack Printing Co., Easton, Pennsylvania (1995) pp. 1409-1410.

Boberg et al., "Etiology and Pathogenesis in Primary Sclerosing Cholangitis", Scand J. Gastroenterol (1994) 29 Suppl. 204:47-58.

Cirillo N.W. and F.R. Zwas., "Ursodeoxycholic Acid in the Treatment of Chronic Liver Disease", Am J Gastroenterol (1994) vol. 89, No. 9 pp. 1447-1452.

K. Einarsson, "Effect of Urodeoxycholic Acid on Hepatic Cholesterol Metabolism", Scand J. Gastroenteral (1994) 29 Suppl. 204:19-23.

S. Friman and J Svarik, "A Possible Role of Ursodeoxycholic Acid in Liver Transplantation", Scand J. Gastroenteral (1994) 29 Suppl. 204:62-4.

A.F. Hofmann, "Pharmacology of Ursodeoxycholic Acid, an Enterohepatic Drug", Scand J. Gastroenteral (1994) 29 Suppl. 204:1-15.

U. Leuschner et al., "Ursodeoxycholic Acid Therapy in Primary Biliary Cirrhosis", Scand J. Gastroenteral (1994) 29 Suppl. 204:40-6.

Lindor et al., "Ursodeoxycholic Acid in the Treatment of Primary Biliary Cirrhosis", Gastroenteral (1994) 106:1284-1290.

McLeod et al., "Glucocorticoid-Dextran Conjugates as Potential Prodrugs for Colon-Specific Delivery: Hydrolysis in Rat Gastrointestinal Tract Contents", J. Pharm Sci., (1994) vol. 83, No. 9., pp. 1284-1288.

McLeod et al., "Glucocorticoid-Dextran Conjugates as Potential Prodrugs for Colon-Specific Delivery: Steady-State Pharamacokinetics in the Rat", Biopharmaceutics & Drug Disposition, (1994) vol. 15, pp. 151-161.

Paumgartner et al., "Ursodeoxycholic Acid Treatment of Cholesterol Gallstone Disease", Scand J. Gastroenterol (1994) 29 Suppl 204: 28-31.

Poupon, et al., "Ursodiol for the Long-Term Treatment of Primary Billary Cirrhosis", The New England Journal of Medicine, (1994) vol. 330, No. 19, pp. 1342-1347.

Drug Name: Tauroursodeoxycholic Acid (TUDCA), TUDCA-Various/UDCA (Ursodiol-Actigall, Watson Pharmaceuticals, Novartis, Generics), 7 pages, 2004.

McLeod et al., "Synthesis and Chemical Stability of Glucocoritcoid-Dextran Esters: Potential Prodrugs for Colon-Specific Delivery", International J. of Pharmaceutics, (1993) vol. 92 pp. 105-114.

Gerrit H. P. Te Wierik et al., "Preparation, Characterization, and Pharmaceutical Application of Linear Dextrins, I. Preparation and Characterization of Amylodextrin, Metastable Amylodextrins, and Metastable Amylose", Pharmaceutical Research, (1993) vol. 10, No. 9 pp. 1274-1279.

Gerritt H. P. Te Wierik et al., "Preparation, Characterization, and Pharmaceutical Application of Linear Dextrins. II. Complexation and Dispersion of Drugs with Amylodextrin by Freeze-Drying and Kneading", Pharmaceutical Research, vol. 10, No. 9 pp. 1280-1284.

G. H. P. Te Wierik et al., "Preparation, Characterization and Pharmaceutical Application of Linear Dextrins: IV. Drug Release from Capsules and Tablets Containing Amylodextrin", International J. of Pharmaceutics, (1993) vol. 98 pp. 219-224.

Scott L. Myers et al., "Solid-State Emulsions: The Effects of Maltodextrin on Microcrystalline Aging", Pharmaceutical Research, (1993) vol. 10, No. 9 pp. 1389-1391.

Roda et al., "Improved Intestinal Absorption of an Enteric-Coated Sodium Ursodeoxycholate Formulation", Pharmaceutical Research, (1994) vol. 11, No. 5 pp. 642-647.

Roda et al., "Influence of Ursodeoxycholic Acid on Biliary Lipids", Scand J Gastroenterol (1994) 29 Suppl. 204:16-8.

A. Stiehl, "Ursodeoxycholic Acid Therapy in Treatment of Primary Sclerosing Cholangitis", Scand J Gastroenterol (1994) 29 Suppl. 204:59-61.

Strandvik et al., "Cystic Fibrosis: Is Treatment with Ursodeoxycholic Acid of Value?", Scand J Gastroenterol (1994) 29 Suppl. 204:65-7.

European Office Action for Application No. 05 820 886.9, 3 pages, Nov. 14, 2008.

M.L. Hanninen, "Sensitivity of *Helicobacter pylori* to Different Bile Salts", Eur. J. Clin. Microbiol. Infect., (1991) vol. 10, pp. 515-518.

Rolandi et al., "Effects of ursodeoxycholic acid (UDCA) on serum liver damage indices in patients with chronic active hepatitis", Eur J. Clin Pharmacol (1991) 40:473-476.

Mathai et al., "The effect of bile acids on the growth and adherence of *Helicobacter pylori*", Aliment Pharmacol Therap. (1991) 5, pp. 653-668.

Tan et al., "Studies on Complexation between β-Cyclodextrin and Bile Salts", International J. Pharmaceutics, (1991) vol. 74 pp. 127-135.

Beuers et al., "Ursodeoxycholic Acid for Treatment of Primary Sclerosing Cholangitis: A Placebo-controlled Trial", Hepatology. (1992) vol. 16, No. 3, pp. 707-714.

Bode et al., "Polymorphism in Helicobacter pylori—a key function in recurrence of infection", Medizinische Klinik, (1992) 87(4):179-84.

Colombo et al., "Ursodeoxycholic Acid Therapy in Cystic Fibrosis-associated Liver Disease: A Dose-response Study", Hepatology, (1992) vol. 16, No. 4 pp. 924-930.

De Caprio et al., "Bile Acid and sterol solubilization in 2-hydroxypropyl-β-cyclodextrin", Journal of Lipid Research, (1992) vol. 33, pp. 441-443.

Fried et al., "Ursodeoxycholic Acid Treatment of Refractory Chronic Graft-versus-Host Disease of the Liver", Annals of Internal Medicine, (1992) 116:624-629.

Walker et al., "Intestinal Absorpotion of Ursodeoxycholic Acid in Patients With Extrahepatic Biliary Obstruction and Bile Drainage", Gastroenterology (1992) 102:810-815.

Dressman et al., "Gastrointestinal Parameters that Influence Oral Medications", J. of Pharmaceutical Sciences, (1993) vol. 82, No. 9 pp. 857-872.

Thorsteinn Loftsson et al., "The Effect of Cyclodextrins on the Solubility and Stability of Medroxyprogesterone Acetate and Megestrol Acetate in Aqueous Solution", International J. of Pharmaceutics, (1993) vol. 98 pp. 225-230.

N. F.H. Ho, "Utilizing Bile Acid Carrier Mechanisms to Enhance Liver an Small Intestine Absorption", Annals New York Academy of Sciences, (1987) 507:315-29.

Aigner A and Bauer A, "Bile acids, Long known active substances with a future", Med Monatsschr Pharm (1988) (11): 369-75.

Dioguardi et al., "The role of oral branched-chain amino acids (BCAAs) in the elevation of plasma ammonia (pNH3)", Chapter 68, in Advances in Ammonia Metabolism and Hepatic Encephalopathy, Soeters et al., eds., (1988) Elsevier Science Publishers B.V., pp. 527-533. 1988.

Montanari et al., "Oral administration of branched-chain amino acids (BCAAs) in liver cirrhosis (LC): effect on their intra- and extracellular pools", Chapter 67, in Advances in Ammonia Metabolism and Hepatic Encephalopathy, Soeters et al., eds., (1988) Elsevier Science Publishers B.V., pp. 519-526.

Fiaccadori et al., "The effect of dietary supplementation with branch-chain amino acids (BCAAs) vs. casein in patients with chronic recurrent portal systemic encephalopathy: a controlled trial", pp. 489-497. (1988) Elsevier Science Publishers B.V. Advances in ammonia metabolism and hepatic encephalopathy.

Podda et al., "Effect of Different Doses of Ursofeoxycholic Acid in Chronic Liver Disease", Digestive Diseases and Sciences, (1989) vol. 34, No. 12, Suppl. pp. 59S-65S.

G. Buck, "Campylobacter pylori and Gastrroduodenal Disease". Clinical Microbiology Reviews, (1990) vol. 3, No. 1 pp. 1-12.

Chazouilleres et al., "Ursodeoycholic Acid for Primary Sclerosing Cholangitis", J. Hepatology, (1990) vol. 11 pp. 120-123.

Colombo et al., "Effects of Ursodeoxycholic Acid Therapy for Liver Disease Associated with Cystic Fibrosis", J. of Pediatrics, (1990) vol. 117, No. 3 pp. 482-489.

M. Y. Morgan, "Branched Chain Amino Acids in the Management of Chronic Liver Disease Facts and Fantasies", J. of Hepatology, (1990) vol. 11 pp. 133-141.

Moses et al., "Insulin Administered Intranasally as an Insulin-Bile Salt Aerosol Effectiveness and Reproducibility in Normal and Diabetic Subjects", Diabetes, (1983) vol. 32 pp. 1040-1047.

Ziv et al., "Bile Salts Facilitate the Absorption of Heparin from the Intestine", Biochemical Pharmacology, (1983) vol. 32, No. 5 pp. 773-776.

K. Müller, "Structural Aspects of Bile Salt-Lecithin Mixed Micelles", Hepatology, (1984) vol. 4, No. 5 pp. 134S-137S.

Murakami et al., "Effect of Bile Salts on the Rectal Absorption of Sodium Ampicillin in Rats", Chem. Pharm. Bull., (1984) vol. 32, No. 5 pp. 1948-1955.

Zentler-Munro et al., "Effect of Intrajejunal Acidity on Aqueous Phase Bile Acid and Lipid Concentrations in Pancreatic Steatorrhoea Due to Cystic Fibrosis", Gut (1984) vol. 25 pp. 500-507.

Gordon et al., "Nasal Absorption of Insulin: Enhancement by Hydrophobic Bile Salts", Proc. Natl. Acad. Sci., (1985) vol. 82 pp. 7419-7423.

Parquet et al., "Bioavailability, Gastrointestinal Transit, Solubilization and Faecal Excretion of Ursodeoxycholic Acid in Man", European J. of Clinical Investigation, (1985) vol. 15 pp. 171-178. 1985.

Stefaniwsky et al., "Ursodeoxycholic Acid Treatment of Bile Reflux Gastritis", Gastroenterology (1985) vol. 89, pp. 1000-1004.

Miyajima et al., "Interaction of β-Cyclodextrin with Bile Salts in Aqueos Solutions", Chem. Pharm. Bull., (1986) vol. 34, No. 3 pp. 1395-1398.

Golub et al., "Physiologic Considerations in Drug Absorption from the Gastrointestinal Tract", J. Allergy Clin. Immunol., (1986) vol. 78, No. 4, Part 2 pp. 689-694.

Van Caekenberghe et al., "In Vitro Synergistic Activity between Bismuth Subcitrate and Various Antimicrobial Agents against Campylobacter pylorids", Antimicrobial Agent and Chemotherapy, (1987) vol. 31, No. 9, pp. 1429-1430.

Carey et al., "Micelle Formation by Bile Salts", Arch Intern Med, (1972) vol. 130, pp. 506-527.

Igimi et al., "pH-Solubility Relations of Chenodeoxycholic and Ursodeoxycholic Acids: Physical-Chemical Basis for Dissimilar Solution and Membrane Phenomena", J. Lipid Research, (1980) vol. 21 pp. 72-90.

Hirai et al., "Effect of Surfactants on the Nasal Absorption of Insulin in Rats", International J. of Pharmaceutics, (1981) vol. 9 pp. 165-172. 1981.

Hirai et al., "Mechanisms for the Enhancement of the Nasal Absorption of Insulin by Surfactants", International J. Phamaceutics, (1981) vol. 9 pp. 173-184.

Hollander et al., "Intestinal Absorption of Aspirin, Influence of pH, Taurocholate, Ascorbate and Ethanol", J. Lab. Clin. Med., (1981) vol. 98, No. 4 pp. 591-595.

Reynier et al., "Comparative Effects of Cholic, Chenodeoxycholic, and Ursodeoxycholic Acids on Micellar Solubilization and Intestinal Absorption of Cholesterol", J. Lipid Research, (1981) vol. 22 pp. 467-473. 1981.

Armstrong et al., "The Hydrophobic-Hydrophilic Balance of Bile Salts. Inverse Correlation between Reverse-Phase High Performance Liquid Chromatographic Mobilities and Micellar Cholesterol-Solubilizing Capacities", J. Lipid Research, (1982) vol. 23 pp. 70-80.

Podda et al., "Gallstone Dissolution After 6 Months of Ursodeoxycholic Acid (UDCA): Effectiveness of Different Doses", J. Int. Med. Res., (1982) vol. 10 pp. 59-63.

Database WPI Section Ch, Week 198824 Derwent Publications Ltd., London, GB, AN-1988-165730 XP002337363 & JP 63104925 A, 1988.

Database WPI Section Ch, Week 198846 Derwent Publications Ltd., London, GB, AN-1988-327783 XP002337364 & JP 63243031 A, 1988.

Remington: The Science and Practice of Pharmacy, Lippincott Williams and Wilkins, pp. 218, 2000.

Kirk et al.; "Inclusion Compounds"; Encyclopedia of Chemical Technology, Fourth Edition; vol. 14; pp. 125-135, 1995.

C.D. Keene et al.; "A Bile Acid Protects Against Motor and Cognitive Deficits and Reduces Striatal Degeneration in the 3-Nitropropionic Acid Model of Huntington's Disease"; Experimental Neurology, vol. 171; pp. 351-360, 2001.

Rodrigues et al. "Neuroprotection by a Bile Acid in an Acute Stroke Model in the Rat" Journal of Cerebral Blood Flow & Metabolism, vol. 22 (pp. 463-471), 2002.

Tanahashi et al., "Treatment of Acute Ischemic Stroke: Recent Progress" Internal Medicine vol. 41, pp. 337-344, 2002.

Ikeda et al., "Antioxidant Nutrients and Hypoxia/Ischemia Brain Injury in Rodents", Toxicology vol. 189, pp. 55-61, 2003.

Ma et al. "Ursodeoxycholic acid inhibits endothelin-1 production in human vascular endothelial cells" European Journal of Pharmacology, vol. 505 (pp. 67-74), 2004.

Chu et al. "Human neural stem cells improve sensorimotor deficits in the adult rat brain with experimental focal ischemia" Brain Research 1016 (pp. 145-153), 2004.

EMEA/CHMP/EWP Workshop; "Slowing the Progression of Neurodegenerative Diseases: Medicinal Productions (MP) Clinical Development"; European Medicines Agency, Pre-authorisation Evaluation of Medicines for Human Use; http://www.emea.europa.eu; pp. 15, Oct. 2, 2006.

International Preliminary Report on Patentability and Written Opinion for International Application No. PCT/US2005/030679 (9 pages), Mar. 6, 2007.

European Office Action for Application No. 04 812 094.3, 8, Applicant: Seo Hong Yoo, 8 pages, Dec. 17, 2007.

Chinese Office Action for Patent Application 01804549.9, 6 pages, Oct. 30, 2008.

Brazilian Office Action for Patent Application PI 9912395-9, 6 pages, Dec. 5, 2008

27th Annual Meeting of the Korean Neurological Association; "Oral Presentation"; Journal of the Korean Neurological Association; vol. 26, Suppl. 2; pp. 3, 2008.

Y. Hattori et al.; "Ursodeoxycholic Acid Inhibits the Induction of Nitric Oxide Synthase"; European Journal of Pharmacology; pp. 147-150, 1996.

C.M.P. Rodrigues et al.; "Bilirubin and Amyloid-β Peptide Induce Cytochrome c Release Through Mitochondrial Membrane Permeabilization"; Molecular Medicine, vol. 6, No. 11; pp. 936-946, 2000.

Deborah F. Gelinas; "Riluzole"; ALS and Other Motor Neuron Disorders,(Suppl 4); pp. 3-4, 2000.

C.M.P. Rodrigues et al.; "The Therapeutic Effects of Ursodeoxycholic Acid as an Anti-Apoptotic Agent"; Expert Opin. Investig. Drugs, vol. 10, No. 7; pp. 1243-1253, 2001.

D. Lapenna et al.; "Antioxidant Properties of Ursodeoxycholic Acid"; Biochemical Pharmacology, vol. 64; pp. 1661-1667, 2002.

N. Shibata et al.; "Molecular Biological Approaches to Neurological Disorders Including Knockout and Transgenic Mouse Models"; Neuropathology, vol. 22; pp. 337-349, 2002.

E. Diguet et al.; "Effects of Riluzole on Combined MPTP + 3-Nitropropionic Acid-Induced Mild to Moderate Striatonigral Degeneration in Mice"; Journal of Neural Transmission; pp. 19, 2004.

G.D. Ghadge et al.; "Mutant Superoxide Dismutase-1-Linked Familial Amyotrophic Lateral Sclerosis: Molecular Mechanisms of Neuronal Death and Protection"; The Journal of Neuroscience, vol. 17, No. 22; pp. 8756-8766, Nov. 15, 1997.

R.E. Castro et al.; "The Bile Acid Tauroursodeoxycholic Acid Modulates Phosphorylation and Translocation of Bad via Phosphatidylinositol 3-Kinase in Glutamate-Induced Apoptosis of Rat Cortical Neurons"; American Society for Pharmacology and Experimental Therapeutics; pp. 34, Jun. 9, 2004.

L. Dupuis et al.; "Evidence for Defective Energy Homeostasis in Amyotrophic Lateral Sclerosis: Benefit of a High-Energy Diet in a Transgenic Mouse Model"; www.pnas.org/cgi/doi/10.1073/pnas.0402026101 ; PNAS, Jul. 27, 2004, vol. 101, No. 30, pp. 11159-11164.

International Preliminary Report on Patentability for International Application No. PCT/US2005/039089 (9 pages), May 10, 2007.

Hofmann et al.; "Bile Acid Solubility and Preperation in Vitro and in Vivo: The Role of Conjugation, pH, and Ca2+ Ions"; Journal of Lipid Research, vol. 33; pp. 617-626, 1992.

Kimura et al.; "A Case of Cerebrotendinous Xanthomatosis: Effects of Ursodeoxycholic Acid Administration on Serum Bile Acids and Cholestanol"; Jap J Med, vol. 21, No. 3; pp. 210-215, Jul. 1982.

Ribatti et al.; "Development of the Blood-Brain Barrier: A Historical Point of View"; The Anotomical Record (Part B: New Anat.); pp. 6, 2006.

Ota et al.; "Metabolism of Bile Acids IV*. Absorption, Distribution, Excretion, and Metabolism of Orally Administered Ursodeoxycholic Acid in Rats"; Hiroshima Journal of Medical Sciences, vol. 26, No. 4; pp. 233-251, Dec. 1977.

C.M.P. Rodrigues et al.; "Neuroprotection by a Bile Acid in an Acute Stroke Model in the Rat"; Journal of Cerebral Blood Flow & Metabolism, vol. 22; pp. 463-471, 2002.

Isreal Office Action; Application No. 181434; pp. 1, Sep. 7, 2009.

Japanese Office Action (w/translation); Application No. 2000-560868; pp. 10, Oct. 9, 2009.

European Office Action; Application No. 05 813 305.9-1216; pp. 16, Jan. 19, 2010.

Kathleen Parfitt: "Martindale: The Complete drug reference, 32nd edition", Pharmaceutical Press, London, UK, pp. 629-630 (Zalcitabine), Jan. 1, 1999.

Kathleen Parfitt: "Martindale: The Complete drug reference, 32nd edition", Pharmaceutical Press, London, UK, pp. 607-609 (Didanosine), Jan. 1, 1999.

Kathleen Parfitt: "Martindale: The Complete drug reference, 32nd edition", Pharmaceutical Press, London, UK, pp. 556-558 (Paclitaxel), Jan. 1, 1999.

Kathleen Parfitt: "Martindale: The Complete drug reference, 32nd edition", Pharmaceutical Press, London, UK, pp. 513-515 (Cisplatin), Jan. 1, 1999.

Kathleen Parfitt: "Martindale: The Complete drug reference, 32nd edition", Pharmaceutical Press, London, UK, pp. 593 (Sumarin), Jan. 1, 1999.

Mitsuyoshi H et al.; "Ursodeoxycholic acid protects hepatocytes against oxidative injury via induction of antioxidants"; Biochemical and Biophysical Research Communications, vol. 263, No. 2; pp. 537-542, ISSN: 0006-291X, Sep. 24, 1999.

Sun Ah Park et al.; "Cisplatin-induced apoptotic cell death in mouse hybrid neurons is blocked by antioxidants through suppression of cisplatin-mediated accumulation of p53 but not of Fas/Fas ligand"; Journal of Neurochemistry, vol. 75, No. 3; pp. 946-953; ISSN: 0022-3042, 2000.

* cited by examiner

FIGURE 1
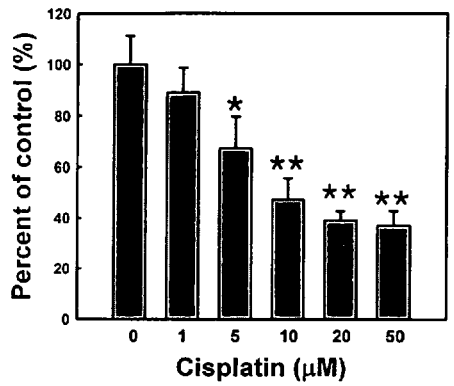
A
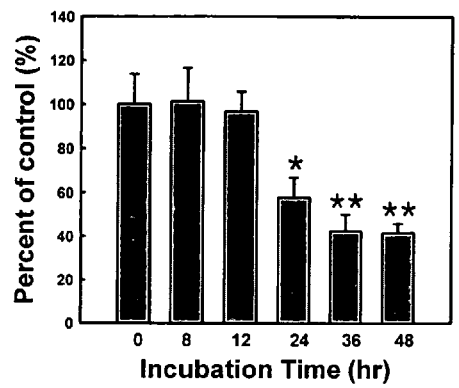
B
FIGURE 2  Control  Cisplatin 10μM  Cisplatin 20μM
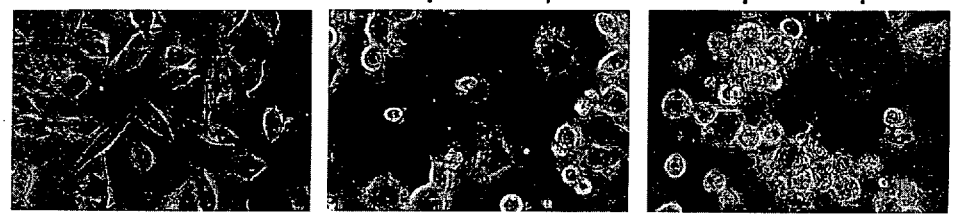
FIGURE 3  Control  Cisplatin 10μM  Cisplatin 20μM
FIGURE 4
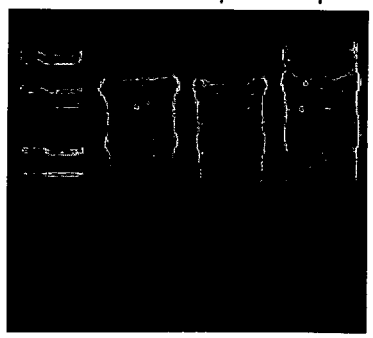

FIGURE 6
A 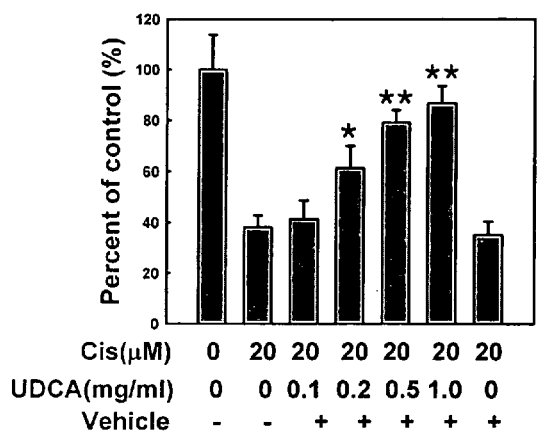
B 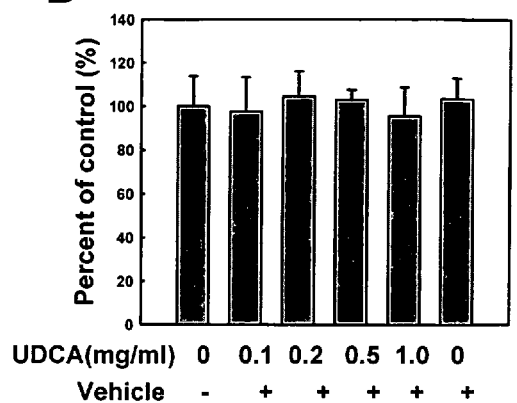
FIGURE 7
Control 
Cisplatin 20μM 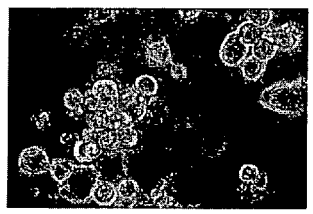
Cisplatin + UDCA 
FIGURE 8
Control 
Cisplatin 20μM 
Cisplatin + UDCA 

FIGURE 10
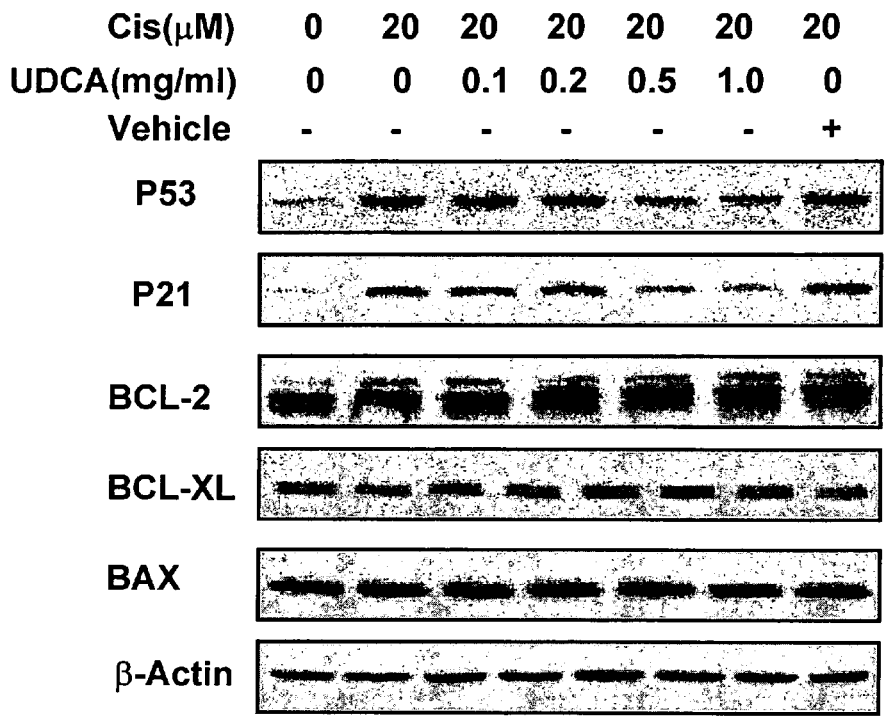
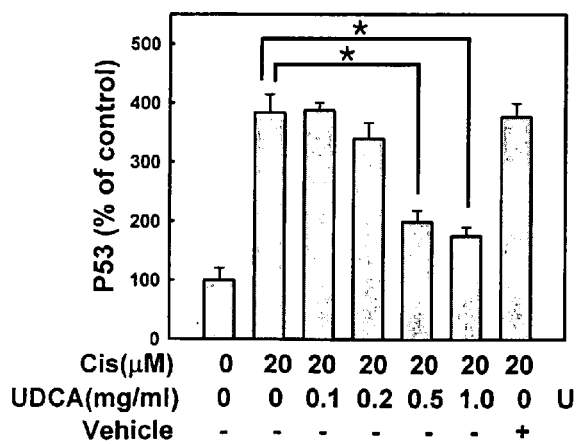
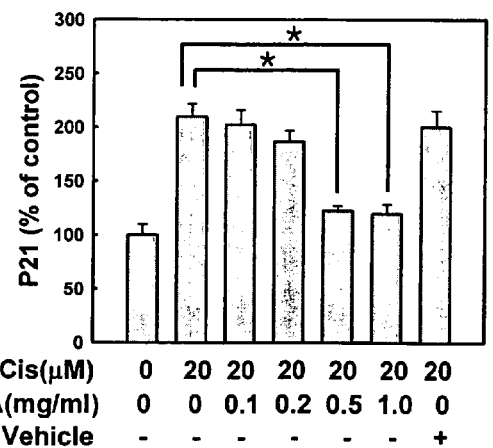

METHODS AND COMPOSITIONS FOR REDUCING TOXICITY OF A PHARMACEUTICAL COMPOUND

CROSS-REFERENCE TO RELATED APPLICATIONS

This application claims the benefit of U.S. Provisional Application Ser. No. 60/619,199 filed Oct. 15, 2004, which is incorporated herein by reference in its entirety.

TECHNICAL FIELD

The present disclosure is related to clear aqueous solutions of one or more bile acids that may be used to ameliorate the toxic effects of a substance (e.g., a chemotherapeutic agent).

BACKGROUND OF THE DISCLOSURE

The full therapeutic value of some pharmaceutical compounds (e.g., medications, drugs) may be difficult or impossible to realize due to off-setting toxic effects. In some cases, one or more toxic effects of a pharmaceutical may be so significant, that the agent cannot be used safely in humans. In other cases, dosages may have to be limited to avoid a toxic effect. In still other cases, the course of therapy may have to be shortened. In addition, exigent circumstances or life-threatening illnesses may compel patients to simply endure such toxic effects to gain a pharmaceutical compound's benefits.

SUMMARY

Therefore, a need has arisen for methods and compositions that ameliorate or eliminate the toxicity of a pharmaceutical compound.

The present disclosure relates to methods and compositions that may ameliorate or eliminate a toxicity (e.g., a toxic effect) of a pharmaceutical compound. For example, a method of ameliorating or eliminating a toxic effect of a pharmaceutical compound may include co-administering the pharmaceutical compound and a bile acid composition. A pharmaceutical compound may, in some embodiments, be selected from the group consisting of chemotherapeutics, stateins, proteosome inhibitors, and antiretroviral agents. In some embodiments, co-administration may include administration of one or more formulations at about the same time or during the same time period. For example, co-administration may include administering both a pharmaceutical compound and a bile acid in a single composition. It may also include simultaneous administration of a plurality of compositions. Alternatively, coadministration may include administration of a plurality of compositions at different times during the same period.

In some embodiments, the present disclosure provides compositions which comprise (1) a bile acid, a bile acid derivative, a bile acid salt, or a bile acid conjugate with an amine, (2) water, and (3) a sufficient quantity of an aqueous soluble starch conversion product such that the bile acid and the starch conversion product remain in solution at any pH within a selected pH range.

The disclosure further relates to a composition which comprises (1) a bile acid, a bile acid derivative, a bile acid salt, or a bile acid conjugate with an amine, (2) water, and (3) a sufficient quantity of an aqueous soluble non-starch polysaccharide such that the bile acid and the polysaccharide remain in solution at any pH within a selected pH range.

The disclosure further relates to a pharmaceutical composition which comprises (1) a bile acid, a bile acid derivative, a bile acid salt, or a bile acid conjugate with an amine, (2) water, (3) a pharmaceutical compound in a pharmaceutically appropriate amount, and (4) a sufficient quantity of an aqueous soluble starch conversion product or an aqueous soluble non-starch polysaccharide such that the bile acid, the pharmaceutical compound, and the carbohydrate remain in solution at any pH level within a selected pH range. According to a non-limiting embodiment of the disclosure, a pharmaceutical compound may be selected from the group consisting of cisplatin, a pharmaceutically active derivative or analog of cisplatin, suramin, a pharmaceutically active derivative or analog of suramin, a chemotherapeutic, a statin, a proteosome inhibitor, and an antiviral agent.

The disclosure further relates to solution dosage forms of bile acid compositions. These dosage forms may have improved bioavailability and absorbability of a bile acid. When these compositions further contain a pharmaceutical compound, the may also have improved bioavailability and absorbability of the pharmaceutical compound.

In some embodiments of the disclosure, a composition is provided which comprises (1) a bile acid, a bile acid derivative, a bile acid salt, or a bile acid conjugate with an amine, (2) water, and (3) a sufficient quantity of carbohydrate such that the bile acid component and the carbohydrate remain in solution at any pH within a selected pH range, wherein the carbohydrate is a combination of an aqueous soluble starch conversion product and an aqueous soluble non-starch polysaccharide. In embodiments containing both soluble non-starch polysaccharide and high molecular weight starch conversion product, the amounts of each are such that when combined together in the composition they are sufficient to allow the bile acid component, the high molecular weight starch conversion product, the soluble non-starch polysaccharide and the pharmaceutical compound, if any, to remain in solution at any pH within a selected pH range.

In some embodiments of the disclosure, a combination therapy composition is provided which may increase the intensity of a response to or efficacy of a pharmaceutical compound. Such a composition may permit administration of lower dosages of a pharmaceutical compound, attack a disease complex at different points, affect elimination and/or alter absorption of a pharmaceutical compound. Such a composition may lead to or contribute to a reduction in toxicity and/or side effects of a pharmaceutical.

BRIEF DESCRIPTION OF THE DRAWINGS

A more complete and thorough understanding of the present embodiments and advantages thereof may be acquired by referring to the following description taken in conjunction with the accompanying drawings, wherein:

FIG. 1A is a bar graph showing the results of a cell viability assay in which N18D3 hybrid neurons were incubated for 48 hours with increasing concentrations cisplatin (* $p<0.05$; ** $p<0.001$ compared with cisplatin treatment);

FIG. 1B is a bar graph showing the results of a cell viability assay in which N18D3 hybrid neurons were incubated with 10 µM cisplatin for the indicated times;

FIG. 2A is a micrograph showing N18D3 hybrid neurons incubated in a control solution;

FIG. 2B is a micrograph showing N18D3 hybrid neurons incubated in a solution containing 10 µM cisplatin;

FIG. 2C is a micrograph showing N18D3 hybrid neurons incubated in a solution containing 20 µM cisplatin;

FIG. 3A is a fluorescence micrograph showing N18D3 hybrid neurons incubated in a control solution and stained with Hoechst 33258;

FIG. 3B is a fluorescence micrograph showing N18D3 hybrid neurons incubated in a solution containing 10 µM cisplatin and stained with Hoechst 33258;

FIG. 3C is a fluorescence micrograph showing N18D3 hybrid neurons incubated in a solution containing 20 µM cisplatin and stained with Hoechst 33258;

FIG. 4 shows size-fractionated DNA from a commercial DNA ladder ("M"), N18D3 neurons incubated in a control solution ("CTL"), in a solution containing 10 µM cisplatin ("Cis 10 µM"), and in a solution containing 20 µM cisplatin ("Cis 20 µM");

FIG. 6A is a bar graph showing the results of a cell viability assay in which N18D3 hybrid neurons were incubated with cisplatin and increasing concentrations of UDCA (* $p<0.05$; ** $p<0.001$);

FIG. 6B is a bar graph showing the results of a cell viability assay in which N18D3 hybrid neurons were incubated with increasing concentrations of UDCA;

FIG. 7A is a micrograph showing N18D3 hybrid neurons incubated in a control solution;

FIG. 7B is a micrograph showing N18D3 hybrid neurons incubated in a solution containing 20 µM cisplatin;

FIG. 7C is a micrograph showing N18D3 hybrid neurons incubated in a solution containing 20 µM cisplatin and 1 mg/mL UDCA;

FIG. 8A is a fluorescence micrograph showing N18D3 hybrid neurons incubated in a control solution and stained with Hoechst 33258;

FIG. 8B is a fluorescence micrograph showing N18D3 hybrid neurons incubated in a solution containing 20 µM cisplatin and stained with Hoechst 33258;

FIG. 8C is a fluorescence micrograph showing N18D3 hybrid neurons incubated in a solution containing 20 µM cisplatin and 1 mg/mL UDCA and stained with Hoechst 33258;

FIG. 10A shows Western blots of N18D3 neurons incubated in a control solution ("Vehicle"), in a solution containing cisplatin ("Cis (µM)"), in a solution containing UDCA ("UDCA (mg/mL)") using antibodies raised against p53, p21, BCL-2, BCL-XL, BAX, and β-actin;

FIG. 10B is a bar graph showing densitometric values of the p53 Western blot of FIG. 10A;

FIG. 10C is a bar graph showing densitometric values of the p21 Western blot of FIG. 10A.

DETAILED DESCRIPTION

Figure 5:
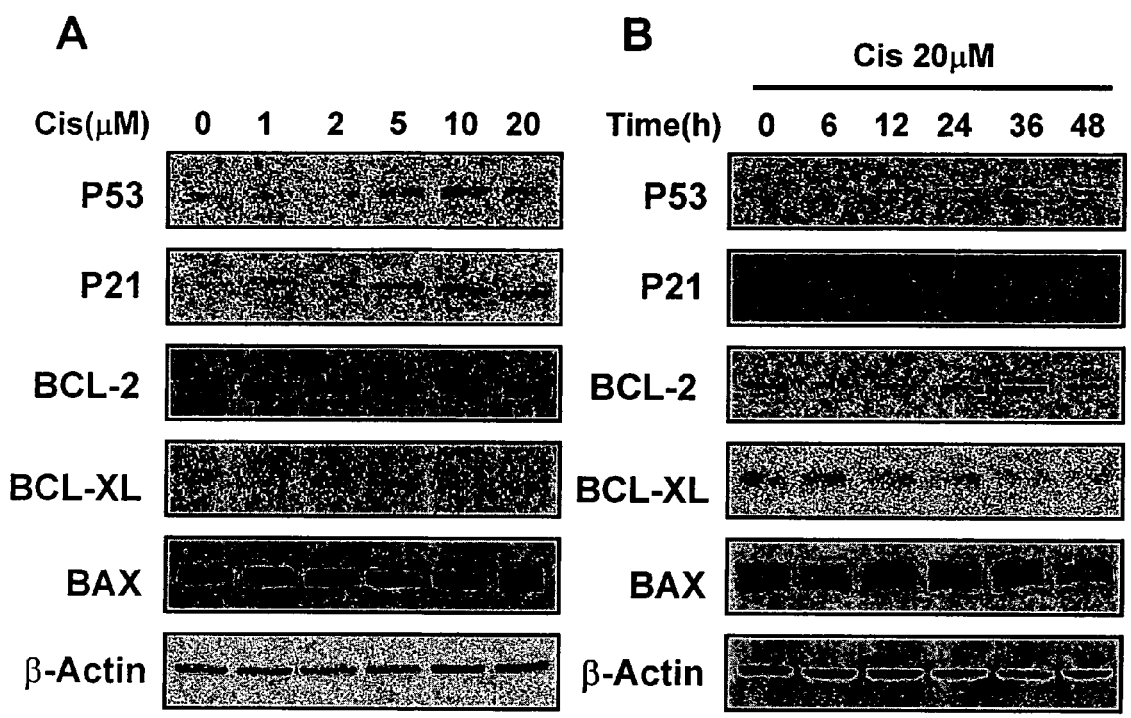
FIG. 5A shows Western blots of N18D3 neurons incubated for 48 hours in a control solution ("0"), in a solution containing cisplatin at a concentration of 1 µM, 2, µM, 5 µM, 5 µM, 10 µM, or 20 µM using antibodies raised against p53, p21, BCL-2, BCL-XL, BAX, and β-actin.
FIG. 5B shows Western blots of N18D3 neurons incubated for the indicated times in 20 µM cisplatin using antibodies raised against p53, p21, BCL-2, BCL-XL, BAX, and β-actin.

The therapeutic benefits of a pharmaceutical compound may be mitigated or even negated if that agent also displays toxicity. For example, although cisplatin and suramin are among the most effective chemotherapeutic agents, they are associated with sensory neuropathy in cancer patients following treatment. A target of cisplatin-induced or suramin-induced neurotoxicity is dorsal root ganglion (DRG) neurons. Animals chronically exposed to cisplatin or suramin exhibit disturbances in axonal transport and microtubule assembly of DRG neurons and apoptotic cell death in DRG neurons. Cisplatin generates oxygen radicals, which are one of the pathogenic intermediates following chemotherapy. Other agents, such as chemotherapeutics, statins, proteosome inhibitors, and antiretroviral agents may similarly target DRG neurons and/or may be associated with axonal degeneration.

While statins may cause peripheral neuropathy, the incidence may be low. In view of the beneficial effects of statins in terms of cardiovascular protection, this incidence may be regarded as relatively innocuous. The incidence of thalidomide neuropathy may be high (e.g., up to three quarters in some series). Although information on dose dependency is variable, lower cumulative doses may be less toxic. Like thalidomide, bortezomib, a novel proteosome inhibitor, is reportedly effective in the treatment of multiple myeloma and is associated with peripheral neuropathy. Oxaliplatin and epothilone are emerging anticancer drugs with neurotoxic potential. Similarly, leflunomide, a new disease modifying-agent approved for the treatment of rheumatoid arthritis, is reported to cause neuropathy. Antiretroviral agents may be associated with antiretroviral toxic neuropathies (ATN), disorders that may be characterized mostly by sensory symptoms that include "dying back" axonal degeneration of long axons in distal regions, loss of unmyelinated fibers, and variable degree of macrophage infiltration in peripheral nerves and dorsal root ganglia. Some antioxidants may effectively protect neurons from neurotoxicity although the mechanism of this neuroprotection has not been established. Cellular factors that may mediate toxicity and/or antioxidant neuroprotection include p53, Fas, and Fas ligand (Fas-L).

Ursodeoxycholic acid (3α-7β-dihydroxy-5β-cholanic acid) ("UDCA"), which may be a major component of bear bile, may be useful as a pharmaceutical compound for the treatment of and the protection against many types of disease (e.g., liver disease). Its medicinal uses may include the dissolution of radiolucent gall stones and treatment of biliary dyspepsia, primarily biliary cirrhosis, primary sclerosing cholangitis, chronic active hepatitis and hepatitis C.

In spite of the extremely valuable therapeutic activities and medical uses of bile acids as therapeutically active agents and as carriers and/or adjuvants, commercial use of bile acids has been limited to pharmaceutical formulations in which the bile acid is present in a solid form (e.g., tablets, capsules, and suspensions). This may be due to the insolubility of bile acids in aqueous media at pH from approximately 1 to 8. Bile has an extremely bitter taste and an equally bitter after-taste that lasts several hours both of which may be due to bile's insolubility. The few aqueous dosage forms that are available are unstable, and have very limited uses because of pH control and maintenance problems. Moreover, some commercial pharmaceutical dosage forms of bile acids have been shown to have scant bioavailability.

The present disclosure provides clear, stable solutions of soluble bile acids that ameliorate or alleviate the toxicity of a pharmacological agent. Solutions of the disclosure may be used as delivery vehicles for a pharmacological agent with one or more toxic effects. Alternatively, solutions of the disclosure may be administered separately, in terms of both the route and time of administration. In some embodiments of the disclosure, a bile composition blocks a toxic effect mediated by p53. In some embodiments of the disclosure, a bile composition blocks a toxic effect mediated by an oxidative process.

In one embodiment, a solution of the disclosure may be used to reduce or eliminate the neurotoxic effect of a pharmaceutical compound (e.g., a chemotherapeutic agent, a statin, a proteosome inhibitor, and an antiretroviral agent) in a human or non-human mammal. Solutions of the disclosure may also reduce or eliminate a toxic effect of an antineoplastic and/or an immunoactive drug (e.g., cisplatin, carboplatin, oxaliplatin, suramin, bleomycin sulfate, azathioprine, azacitidine, busulfan, doxorubicin hydrochloride, paclitaxel, mitomycin, epothilone, colchicine, metronidazole, sapsone, misonidazole, sulfasalazine, disulfiram, nitrofurantoin, tacrolimus nucleoside analogs, taxanes, gangliosides, vincristine, penicillamine, thalidomide, vidarabine, isoniazid, vincaalkaloids, amiodarone, perhexiline, and leflunomide), a proteosome inhibitor (e.g., bortezomib), an antiretroviral agent (e.g., didanosine, zalcitabine, stavudine, lamivudine), and/or a hydroxymethyl glutaryl coenzyme A reductase inhibitor (e.g. Prevastatin, lovastatin, simvastatin, fluvastatin, rosuvastatin).

The present disclosure relates to an aqueous solution comprising (i) one or more soluble bile acids, aqueous soluble bile acid derivatives, bile acid salts, or bile acid conjugated with an amine, (collectively "bile acid"), (ii) water, and (iii) one or more aqueous soluble starch conversion products or aqueous soluble non-starch polysaccharides in an amount sufficient to produce a solution which does not form a precipitate at any pH within a desired pH range. The composition may contain a bile acid or a bile acid salt which itself has pharmaceutical effectiveness. Formulations of the disclosure may act as a carrier, an adjuvant or enhancer for the delivery of a pharmaceutical material which remains dissolved in the composition of the disclosure across the desired pH range. Alternatively, according to some embodiments of the disclosure, the composition may comprise a non-bile acid pharmaceutical that is incompletely soluble.

In some embodiments, it may be an advantage that the bile acid and the carbohydrate remain in solution without precipitation at any pH from acidic to alkaline. These aqueous solution systems of bile acid are substantially free of precipitate or particles. A further advantage of this disclosure is that the aqueous solution systems demonstrate no changes in physical appearance such as changes in clarity, color or odor following the addition of strong acids or alkali even after several months observation under accelerated conditions of storage at 50° C.

In some embodiments of the disclosure, an aqueous solution system of bile acid is administered orally whereupon it reaches the intestine through the gastrointestinal track without precipitation of bile acids by exposure to acidic gastric juices and alkaline juices of the intestine. These dissolved bile acid formulations demonstrate intact solution systems in the intestine can be effectively and completely absorbed and, consequently, undergo enterohepatic cycling. According to an embodiment of the disclosure, bile acid solubility (e.g. precipitation and changes in physical appearance) is affected by whether a carboxylic acid side chain of certain bile acids can be protonated (non-ionized), is ionized, or is a simple carboxylic acid.

The ionization state of a bile acid carboxylic acid side chain greatly effects the hydrophobicity and the hydrophillicity of the bile acid in these aqueous solution systems. In some embodiments of the disclosure, that ionization state is manipulated by adjusting the pH to control the toxicity, absorption, and amphiphilicity of bile acids. One or more bile acids may be dissolved in these aqueous solution systems as a therapeutically active agent, as an adjuvant of a drug, as a carrier of a drug or as an enhancer of drug solubility. These aqueous solution systems may be prepared for oral consumption, enemas, mouthwashes, gargles, nasal preparations, otic preparations, injections, douches, topical skin preparations, other topical preparations, and cosmetic preparations which have a desired pH without the disadvantage of precipitation or deterioration in physical appearance after long periods of time.

Soluble bile acids are any type of aqueous soluble bile acids. A bile acid salt is any aqueous soluble salt of a bile acid. Bile salts exhibit greater solubilizing capacity for phospholipid and cholesterol and are consequently better detergents. More hydrophobic bile salts may be more injurious to various membranes, both in vivo and in vitro. Aqueous dissolved salts of bile acids may be formed by the reaction of bile acids described above and an amine including but not limited to aliphatic free amines such as trientine, diethylene triamine, tetraethylene pentamine, and basic amino acids such as arginine, lysine, ornithine, and ammonia, and amino sugars such as D-glucamine, N-alkylglucamines, and quaternary ammonium derivatives such as choline, heterocyclic amines such as piperazine, N-alkylpiperazine, piperidine, N-alkylpiperidine, morpholine, N-alkylmorphline, pyrrolidine, triethanolamine, and trimethanolamine. According to the disclosure, aqueous soluble metal salts of bile acids, inclusion compound between the bile acid and cyclodextrin and its derivatives, and aqueous soluble O-sulfonated bile acids are also included as soluble bile acid salts.

Soluble bile acid derivatives, according to some embodiments of this disclosure, may be those derivatives which are in aqueous solution as soluble as or more soluble than is the corresponding underivatized bile acid. Bile acid derivatives include, but are not limited to derivatives formed at the hydroxyl and carboxylic acid groups of the bile acid with other functional groups including but not limited to halogens and amino groups. Soluble bile acid may include an aqueous preparation of a free acid form of bile acid combined with one of HCl, phosphoric acid, citric acid, acetic acid, ammonia, or arginine.

Bile acids that may be used in accordance with the teachings of this disclosure include, without limitation, ursodeoxycholic acid, chenodeoxycholic acid, cholic acid, hyodeoxycholic acid, deoxycholic acid, 7-oxolithocholic acid, lithocholic acid, iododeoxycholic acid, iocholic acid, tauroursodeoxycholic acid, taurochenodeoxycholic acid, taurodeoxycholic acid, taurolithocholic acid, glycoursodeoxycholic acid, taurocholic acid, glycocholic acid, and their derivatives at a hydroxyl or carboxylic acid group on the steroid nucleus.

In some embodiments of the instant disclosure, a major advantage may be that delivery of bile acid in solution achieves higher in vivo levels of bile acids than conventional preparations. Therefore, the therapeutic potential of bile acid may be more fully achieved than previous formulations. The in vivo levels of bile acids attainable with existing formulations in which bile is incompletely solubilized are lower and require administration of larger amounts of bile acids. Since bile acid is completely dissolved in the inventive formulations, higher in vivo levels of bile acid may be achieved, even though lower doses are administered.

In some embodiments of the disclosure, a plurality of bile acids may be used in a single formulation. Mixtures of two or more bile salts of differing hydrophobic activity may behave as a single bile salt of an intermediate hydrophobic activity. As a result, detergent properties and the toxicity of mixtures of two bile acids of differing hydrophobic activity often are intermediate between the individual components.

Mixtures of two or more bile salts of differing hydrophobic activity may behave as a single bile salt of an intermediate hydrophobic activity. As a result, detergent properties and the toxicity of mixtures of two bile acids of differing hydrophobic activity often are intermediate between the individual components.

Carbohydrates suitable for use in the disclosure include aqueous soluble starch conversion products and aqueous soluble non-starch polysaccharides. According to some embodiments of the present disclosure, aqueous soluble starch conversion products include carbohydrates obtained directly from the partial or incomplete hydrolysis of starch under various pH conditions. Non-limiting examples include maltodextrin, dextrin, liquid glucose, corn syrup solid (dried powder of liquid glucose), and soluble starch, preferably maltodextrin or corn syrup solid, most preferably corn syrup solid. For example, MALTRIN® M200, a corn syrup solid, and MALTRIN® M700 a maltodextrin, both of which are manufactured by GPC®, Grain Processing Corporation of Muscatine, Iowa, may be used. For the purpose of this embodiment, the term "corn syrup" includes both corn syrup and liquid glucose. If a starch conversion product is polymeric, the polymer has at least one reducing end and at least one non-reducing end and may be linear or branched. The molecular weight may be from about 100 mass units to over 106 mass units. High molecular weight aqueous soluble starch conversion products are those having a molecular weight over 105.

According to some embodiments of the present disclosure, aqueous soluble non-starch polysaccharides may be under various pH conditions by various hydrolytic or synthetic mechanisms. Non-limiting examples include to dextran, guar gum, pectin, indigestible soluble fiber. If polymeric, the polymer has at least one reducing end and at least one non-reducing end. The polymer may be linear or branched. The molecular weight is from about 100 mass units to over 106 mass units. Preferably the molecular weight is over 105 mass units.

The amount of high molecular weight aqueous soluble starch conversion product and/or soluble non-starch polysaccharide used in embodiments of the disclosure is at least the amount needed to render the chosen bile acid(s) in the preparation soluble in the concentration desired and in the pH range desired. In some embodiments of the disclosure, the approximate minimal weight ratio of maltodextrin to UDCA required to prevent UDCA precipitation is 6:1 (i.e. 1.2 g for every 0.2 g of UDCA, 6 g for every 1 g of UDCA, and 12 g for every 2 g of UDCA in 100 mL of water). In some embodiments of the disclosure, the approximate minimal quantity of maltodextrin is 30 g for every 200 mg of chenodeoxycholic acid, 12 g for every 200 mg of 7-ketolithocholic acid, 10 g for every 200 mg of cholic acid and 50 g for every 200 mg of deoxycholic acid. In some embodiments of the disclosure, the approximate minimal weight ratio of liquid glucose (commercial light corn syrup) to UDCA required to prevent the precipitation of bile acids from the aqueous solution dosage forms of the disclosure is about 25:1 (i.e. 12.5 g for every 500 mg UDCA in 100 mL water and 25 g for every 1 g ursodeoxycholic acid in 200 mL water). In some embodiments of the disclosure, the approximate minimal quantity of dried powder of liquid glucose (corn syrup solid, e.g. MALTRIN® M200) required to prevent the precipitation of bile acids from the aqueous solution dosage forms of the disclosure is 30 g for every 1 g ursodeoxycholic acid in 100 mL water, and approximately 60 g for every 2 g of ursodeoxycholic acid in 200 mL water. In some embodiments of the disclosure, the approximate minimal quantity of soluble non-starch polysaccharide required to prevent the precipitation of bile acids from the aqueous solution dosage forms of the disclosure is 50 g guar gum for every 500 mg ursodeoxycholic acid in 100 mL water and 80 g of pectin for every 500 mg of ursodeoxycholic acid in 100 mL water. The minimal required quantity of high molecular weight aqueous soluble starch conversion products or soluble non-starch polysaccharide is primarily determined by the absolute quantity of bile acids in the solution formulation rather than the concentration.

In some embodiments of the disclosure, a formulation may comprise cyclodextrin in addition to a starch conversion product and/or a non-starch polysaccharide.

In some embodiments of the disclosure, the formulation further comprises dietary fiber. Non-limiting examples of dietary fiber include guar gum, pectin, psyllium, oat gum, soybean fiber, oat bran, corn bran, cellulose and wheat bran.

In some embodiments of the disclosure, the formulation further comprises emulsifying agents. For the purpose of the disclosure, the term "emulsifying agent" includes emulsifying agents and suspending agents. Non-limiting examples of emulsifying agents include guar gum, pectin, acacia, carrageenan, carboxymethyl cellulose sodium, hydroxymethyl cellulose, hydroxypropyl cellulose, methyl cellulose, polyvinyl alcohol, povidone, tragacanth gum, xanthan gum, and sorbitan ester.

The selected pH range for which the formulation will not precipitate its bile acid, starch conversion product, soluble non-starch polysaccharide or its pharmaceutical compound may be any range of pH levels obtainable with an aqueous system. Preferably this range is between about pH 1 and about pH 14 and more preferably between about pH 1 and about pH 10. Still more preferably the range is any subset of the range of pH levels obtainable in an aqueous system sufficient for a pharmaceutical formulation to remain in solution from preparation, to administration, to absorption in the body, according to the method of administration. Thus, the composition may be used as a pharmaceutical formulation wherein the pharmaceutical compound remains in solution without precipitation at prevailing pH levels in the mouth, stomach and intestines. In some embodiments of the disclosure, a bile acid remains dissolved under acidic conditions as a free bile acid in spite of the general insolubility of bile acids under acidic conditions.

In some embodiments of the disclosure, the pharmaceutical is cisplatin. Non-limiting examples of other pharmaceutical compounds include hormones, hormone antagonists, analgesic, antipyretics, anti-inflammatory drugs, immunoactive drugs, antineoplastic drugs, antibiotics, anti-inflammatory agents, sympathomimetic drugs, anti-infective drugs, anti-tumor agents, and anesthetics. Further non-limiting examples include drugs that target or effect the gastrointestinal tract, liver, cardiovascular system, and respiratory system. Further non-limiting examples of pharmaceutical compounds include insulin, heparin, calcitonin, ampicillin, octreotide, sildenafil citrate, calcitriol, dihydrotachysterol, apomorphine, yohimbine, trazadone, acyclovir, amantadine•HCl, rimantadine•HCl, cidofovir, delavirdine•mesylate, didanosine, famciclovir, foscarnet sodium, fluorouracil, ganciclovir sodium, idoxuridine, interferon-α, lamivudine, nevirapine, penciclovir, ribavirin, stavudine, trifluridine, valacyclovir•HCl, zalcitabine, zidovudine, indinavir•H$_2$SO$_4$, ritonavir, nelfinavir•CH$_3$SO$_3$H, saquinavir•CH$_3$SO$_3$H, d-penicillamine, chloroquine, hydroxychloroquine, aurothioglucose, gold sodium thiomalate, auranofin levamisole, dacarbazine, isoprinosine, methyl inosine monophosphate, muramyl dipeptide, diazoxide, hydralazine•HCl, minoxidil, dipyridamole, isoxsuprine•HCl, niacin, nylidrin•HCl, phentolamine, doxazosin•CH$_3$SO$_3$H, prazosin•HCl, terazocin•HCl, clonidine•HCl, nifedipine, molsidomine, amiodarone, acetylsalicylic acid, verapamil, diltiazem, nisoldipine, isradipine, bepridil, isosorbide•dinitrate, pentaerythrytol•tetranitrate, nitroglycerin, cimetidine, famotidine, nizatidine, ranitidine, lansoprazole, omeprazole, misoprostol, sucralfate, metoclopramide•HCl, erythromycin, bismuth compound, alprostadil, albuterol, pirbuterol, terbutaline•H$_2$SO$_4$, salmetrol, aminophylline, dyphylline, ephedrine, ethylnorepinephrine, isoetharine, isoproterenol, metaproterenol, nedocromil, oxtriphylline, theophylline, bitolterol, fenoterol, budesonide, flunisolide, beclomethasone•dipropionate, fluticasone•propionate, codeine, codeine sulfate, codeine phosphate, dextromethorphan•HBr, triamcinolone•acetonide, montelukast sodium, zafirlukast, zileuton, cromolyn sodium, ipratropium bromide, nedocromil sodium benzonate, diphenhydramine•HCl, hydrocodone•bitartarate, methadone•HCl, morphine sulfate, acetylcysteine, guaifenesin, ammonium carbonate, ammonium chloride, antimony potassium tartarate, glycerin, terpin•hydrate, colfosceril palmitate, atorvastatin•calcium, cervastatin•sodium, fluvastatin•sodium, lovastatin, pravastatin•sodium, simvastatin, picrorrhiza kurroa, andrographis paniculata, moringa oleifera, albizzia lebeck, adhatoda vasica, *curcuma longa, momordica charantia, gymnema sylvestre*, terminalia arjuna, azadirachta indica, tinosporia cordifolia, metronidazole, amphotericin B, clotrimazole, fluconazole, haloprogin, ketoconazole, griseofulvin, itraconazole, terbinafin•HCl, econazole•HNO$_3$, miconazole, nystatin, oxiconazole•HNO$_3$, sulconazole•HNO$_3$, cetirizine•2HCl, dexamethasone, hydrocortisone, prednisolone, cortisone, catechin and its derivatives, glycyrrhizin, glycyrrhizic acid, betamethasone, fludrocortisone•acetate, flunisolide, fluticasone•propionate, methyl prednisolone, somatostatin, lispro, glucagon, proinsulin, insoluble insulins, acarbose, chlorpropamide, glipizide, glyburide, metformin•HCl, repaglinide, tolbutamide, amino acid, colchicine, sulfinpyrazone, allopurinol, piroxicam, tolmetin sodium, indomethacin, ibuprofen, diflunisal, mefenamic acid, naproxen, and trientine.

Additional examples of pharmaceutical compounds that may be included in the formulation are any compounds which remain soluble when added to the formulation. With an additional pharmaceutical compound in the formulation, a bile acid in solution may act as an adjuvant, carrier, or enhancer for the solubility of certain therapeutically active agents, including, but not limited to, insulin (pH 7.4-7.8), heparin (pH 5-7.5), calcitonin, ampicillin, amantadine, rimantadine, sildenafil, neomycin sulfate (pH 5-7.5), apomorphine, yohimbine, trazadone, ribavirin, paclitaxel and its derivatives, retinol, and tretinoin, which are soluble and stable in acid and/or alkali and can be added as needed into these aqueous solution dosage forms of certain concentrations of bile acids in this disclosure. Certain therapeutically active agents, including, but not limited to, metformin HCl (pH 5-7), ranitidine HCl, cimetidine, lamivudine, cetrizine 2HCl (pH 4-5), amantadine, rimantadine, sildenafil, apomorphine, yohimbinee, trazadone, ribavirin and dexamethasone, hydrocortisone, prednisolone, triamcinolone, cortisone, niacin, taurine, vitamins, naturally occurring amino acids, catechin and its derivatives, glycyrrhizal extract and its main constituents such as glycyrrhizin and glycyrrhizic acid, water soluble bismuth compounds (e.g., bismuth sodium tartrate), and which are soluble and stable in acid and/or alkali can be added as needed into these aqueous solution dosage formulations containing ursodeoxycholic acid in this disclosure.

Some embodiments of the disclosure may be practiced with pH adjustable agents. Non-limiting examples include HCl, H$_3$PO$_4$, H$_2$SO$_4$, HNO$_3$, CH$_3$COOH, citric acid, malic acid, tartaric acid, lactic acid, phosphate, eidetic acid and alkalies.

In some embodiments of the disclosure, the formulations may be used to treat human and mammalian diseases. The disclosure contemplates treating gastrointestinal disorders, liver diseases, gall stones, and hyperlipidemia. Non-limiting examples of liver diseases include alcohol-induced liver diseases and non-alcohol-induced liver diseases. Non-limiting examples of gastrointestinal disorders include chronic gastritis, reflux gastritis, and peptic ulcer disease. Non-limiting examples of non-alcohol-induced liver diseases include primary biliary cirrhosis, acute and chronic hepatitis, primary sclerosing cholangitis, chronic active hepatitis, and excess accumulation of fat in the liver. The disclosure further contemplates treating viral, bacterial and fungal diseases. In some embodiments of the disclosure, a formulation is administered to treat and/or eradicate *Helicobacter pylori* infection. In some embodiments of the disclosure, a formulation is administered to treat and/or eradicate hepatitis C virus infection, influenza A, Influenza C, parainfluenza 1, sendai, rubella, and pseudorabies virus. In some embodiments of the disclosure, a formulation is administered to treat acute or chronic inflammatory diseases. Non-limiting examples of inflammatory diseases include bronchitis, chronic pharyngitis, and chronic tonsillitis. In some embodiments of the disclosure, a formulation is administered to treat hypercholersterolemia.

In some embodiments of the disclosure, the formulation is modified such that it may be administered as a liquid, solid, powder or tablet. In some embodiments of the disclosure, the formulation is comprised in a solution, syrup, thick syrup or paste. A non-limiting example of a solution is a solution of maltodextrin wherein the concentration of maltodextrin is less than 500 g/L. A non-limiting example of a syrup is a solution of maltodextrin wherein the concentration of maltodextrin is between 500 g/L and 1.0 kg/L inclusive. A non-limiting example of a thick syrup is a solution of maltodextrin wherein the concentration of maltodextrin is between 1.0 kg/L and 1.2 kg/L inclusive. A non-limiting example of a paste is a solution of maltodextrin wherein the concentration of maltodextrin is greater than 1.2 kg/L.

The stability of dosage formulations of the disclosure may be evaluated by measuring the concentration of the relevant bile acid over time in preparations comprising soluble bile acid, a high molecular weight aqueous soluble starch conversion product, and water at various pH and temperature levels. The retention time (high performance liquid chromatography) of each bile acid may be adjusted as needed to permit individual analysis each bile acid present in complex samples, i.e. a sample having a plurality of bile acids. Stability tests may also be performed by assessing the light-scattering properties of a test solution. In addition, established accelerated testing conditions may be used.

All stability tests performed on solutions of the disclosure were satisfactory in that the concentration of bile acid as measured by HPLC did not change appreciably over time at various pH levels. Particularly, all bile acid solution formulations tested showed excellent results in the stability tests with no precipitation and no physical appearance changes over the test period. Some formulations remain stable for over 2 years. The aqueous solution dosage forms according to this disclosure that were tested did not change either physically or chemically at various pH conditions under the accelerated conditions despite the addition of therapeutically and chemically active agents that are stable and soluble in hydrochloric acid solution. Therefore, these aqueous solution systems may be extremely valuable pharmaceutical dosage forms for the therapeutically active bile acids preparations, and/or the drug (pharmaceutical compound) delivery preparations in which bile acids play roles as the adjuvant of drug, the carrier of drug, or the enhancer of solubility of a drug by micelle formation at various pH conditions without the stability problems, including precipitation in acidic conditions.

EXAMPLES

The present disclosure may be better understood from the following examples. However, one skilled in the art will readily appreciate the specific materials, compositions, and results described are merely illustrative of the disclosure, and are not intended to, nor should be construed to, limit the scope disclosure and its various embodiments.

Example 1

Preparation of Bile Acid Solutions

A stock solution of bile acid was prepared by first dissolving UDCA (60 g) in 500 mL NaOH (6.7 g) solution. Next, to the resulting clear solution, 375 g of maltodextrin was added, portion by portion with vigorous agitation. The pH was then adjusted to between 7.0 and 7.2 by the dropwise addition of HCl with high throughput sonication (750 W, 20 kHz). The volume was then adjusted to 1.0 L with injectable distilled water. Lastly, the resulting clear solution was filter sterilized using a 0.22 µGP express plus membrane under aseptic conditions. Dilutions of this solution to the desired UDCA concentration were prepared according to standard pharmacy practice.

Example 2

Characterization of N18D3 Hybrid Neuronal Cell Line

The stable N18D3 mouse hybrid neuron line was used as a model neuronal cell culture system to investigate the pathomechanisms involved in cisplatin-induced neuropathy. This cell line is a hybrid between a mouse DRG neuron isolated from four-week-old Balb/C mice and the mouse neuroblastoma cell line N18TG2. N18D3 cells were grown in a 6-cm dish with Dulbecco's modified Eagle's medium containing 5% fetal bovine serum and 5% horse serum and incubated at 37° C. in a humidified atmosphere with 5% $CO_2$.

Clonal N18D3 cells exhibited neuron-like properties not displayed by the parental neuroblastoma. For example, N18D3 hybrid neurons express a specific immunoreactivity to high molecular weight neurofilament protein (NF—H), indicating that they carry neuron-specific phenotypes. N18D3 hybrid neurons also expressed microtubule-associated protein-2 and low and medium molecular weight neurofilaments as shown by immunocytochemistry and sodium channel activity as shown by whole-cell clamp experiments.

Example 3

MTT Assay

Cell viability was assessed by measurement of 3-(4,5-Dimethylthiazol-2-yl)-2,5 diphenyltetrazolium bromide (MTT) reduction, which is an indicator of the pyridine nucleotide redox state of the cells. N18D3 cells ($1 \times 10^5$) were seeded onto 96-well plates in 0.1 ml of medium and twenty-four hours later were exposed to cisplatin and/or UDCA solutions according to Example 1. Cells were then incubated for pre-selected periods of time in the presence of cisplatin, UDCA, or both.

Ten microliters of MTT solution [5 mg/ml in phosphate-buffered saline (PBS)] was added to each well, and then the plates were incubated for 3 h at 37° C. After elution of the dye with dimethyl sulfoxide (Sigma), absorbance at 570 nm was measured in a dual-beam microtiter plate reader with 630-nm reference.

Example 4

Nuclear Staining with Hoechst 33258

N18D3 cells grown on coverslips were treated with cisplatin for pre-selected times, fixed with 4% paraformaldehyde (pH 7.4) for 10 min, washed with PBS three times, and then incubated with 10 µg/ml Hoechst 33258 in PBS for 10 min. Changes in nuclear morphology were examined under an Olympus confocal fluorescence microscope.

Example 5

DNA Fragmentation Analysis

Total DNA was extracted from the N18D3 hybrid neurons exposed to cisplatin or to cisplatin plus a 0.1 mg/mL UDCA solution prepared according to Example 1. To analyze DNA fragmentation patterns, cells were lysed in 5 mM Tris-HCl, pH 7.4, containing 0.5% TritonX-100 and 20 mM EDTA. Lysates were centrifuged at 16,090 g for 15 min at 40° C. Supernatants were extracted with phenol-choloroform-isoamyl alcohol (25:24:1), precipitated in ethanol containing 0.3 M sodium acetate, and resuspended in Tris-EDTA buffer. The soluble DNA samples were subjected to electrophoresis on a 1.2% agarose gel.

Example 6

Cisplatin Induces Apoptotic Cell Death in N18D3 Hybrid Neurons

Figure 9:
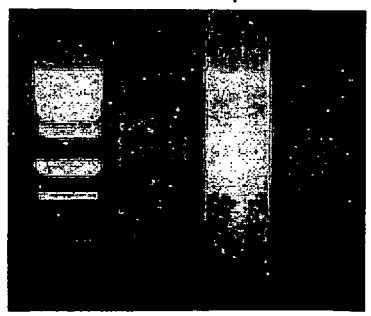
FIG. 9 shows size-fractionated DNA from a commercial DNA ladder ("M"), N18D3 neurons incubated in a control solution ("CTL"), in a solution containing 20 µM cisplatin ("Cis 20 µM"), and in a solution containing 20 µM cisplatin and 1 mg/mL UDCA ("Cis+UDCA")

Cisplatin treatment of N18D3 neurons induced cytotoxicity in a dose- and time-dependent manner, as determined according to the MTT reduction assay of Example 3 (FIGS. 1A, 1B, 6A and 6B). Following exposure to 20 µM cisplatin for 36 h, cell viability decreased to 40% of untreated control cells (FIG. 1A) Cisplatin induced cell death in N18D3 neurons with morphological changes such as cell shrinkage and cytoplasmic blebbing (FIGS. 2B, 2C, and 7B). N18D3 neurons exposed to cisplatin also showed condensed and fragmented nuclear changes, characteristic of apoptotic cell death, as shown by staining with Hoechst 33258 according to Example 4 (FIGS. 3B, 3C, and 8B). Moreover, cisplatin induced a clear 180- to 200-base internucleosomal DNA cleavage after cisplatin treatment according to the DNA fragmentation assay of Example 5 (FIGS. 4 and 9). These findings suggest that, without limiting the present disclosure to any particular mechanism of action, cisplatin-induced cytotoxicity in N18D3 hybrid neurons results from a cisplatin-mediated apoptotic pathomechanism.

Example 7

UDCA Solution Substantially Reduced Cisplatin-Induced Apoptotic Cell Death in N18D3 Hybrid Neurons N18D3 hybrid neurons were pretreated with a bile solution according to Example 1 for one hour prior to cisplatin treatment. Viability of neurons exposed to 20 µM cisplatin after being pretreated with a bile solution (1 mg/mL UDCA) was significantly increased as assessed by the MTT assay of Example 3 (FIG. 6A) Pretreatment with a control solution prepared according to Example 1 except lacking UDCA had no effect on viability in the presence of cisplatin (right-most bar, FIG. 6A). In addition, bile solutions according to Example 1 had no adverse effect on cell viability as measured by MTT assay (FIG. 6B).

Moreover, N18D3 hybrid neurons pretreated with the bile solution displayed fewer cisplatin-induced morphological changes such as cell shrinkage and cytoplasmic blebbing (FIG. 7C) and no condensed or fragmented nuclear morphology (FIG. 8C). Bile-pre-treated N18D3 hybrid neurons exposed to cisplatin for 36 hours lacked the internucleosomal DNA fragmentation observed in cells exposed to cisplatin without bile pre-treatment.

In this Example, the optimal concentration of UDCA for alleviating cisplatin-induced neurotoxicity was 1 mg/mL (equivalent to 0.1 mM of UDCA).

Example 8

Western Blot Analysis

N18D3 hybrid neurons were washed with PBS and lysed in RIPA buffer (50 nM Tris-HCl, pH 8.0, 150 mM NaCl, 1% NP-40, 0.5% sodium ceoxycholate, 0.1% sodium docecy sulfate containing 1 mM phenylmethylsulfonyl fluoride, and 1 µg/mL pepstatin A) on ice for 15' minutes. Cell lysates were cleared by centrifugation at 18,890 g for 15 minutes. Forty micrograms of protein, as determined by the Bio-Rad protein assay, was electrophoresed through 12% acrylamid-sodium dodecyl sulfate denaturing gels. Gels were transferred to Immobilon (Millipore, Bedford, Mass.) and probed with antibodies as recommended by the suppliers. Detection of specific protein was performed using an enhanced chemiluminiscence system.

Example 9

Bile Acid Solutions Block Accumulation of p53 and p21

Figure 11:
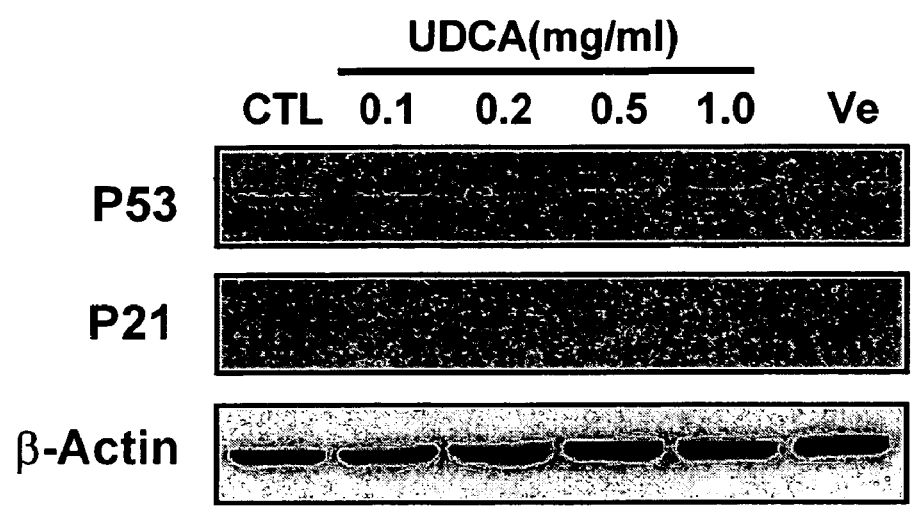
FIG. 11 shows Western blots of N18D3 neurons incubated in a control solution containing 20 µM cisplatin without pre-treatment ("CTL"), with pre-treatment in a solution lacking UDCA ("Ve"), or with pre-treatment in a solution having the indicated amount of UDCA.

Key effector molecules and the regulatory mechanisms by which bile solutions exert neuroprotective effects in N18D3 hybrid neurons were investigated by assessing the expression of various proteins previously implicated in apoptosis was determined. Accumulation of p53 protein increased four hours after treatment with 20 µM cisplatin, reached maximal level at twenty-four hours, and then slightly declined thereafter (FIG. 5B). By contrast, bile-pre-treated neurons exhibit substantially less accumulation of p53 protein (FIGS. 10A, 10B, and 11).

These results are in accord with the results discussed in Examples 6 and 7, including the same optimal concentration of UDCA, namely 1 mg/mL. Without restricting the disclosure to any particular mechanism of action, these results suggest that cisplatin-induced accumulation of p53 is one of major causes of apoptotic cell death of neurons and that suppression of p53 accumulation by bile solutions is a key requirement for neuroprotection.

In parallel with these p53 expression data, p21, a downstream target of activated p53, increased after four hours of cisplatin treatment, peaked at 8 hours, and declined thereafter, perhaps due to caspase activity. The bile acid solutions of Example 1 significantly suppressed accumulation of p21 (FIGS. 10A, 10C, and 11). This result is also in accord with he results of Examples 6 and 7, including the same optimal concentration of UDCA, namely 1 mg/mL.

In contrast, other downstream gene products of p53 including Bcl-2, Bcl-XL and Bax (Bcl2-associated X protein) showed no change in their expression following cisplatin treatment (FIG. 10A). Again, without limiting the disclosure to any particular model, taken together, these results suggest that cisplatin-induced apoptosis is closely associated with p53 activation in neurons and that bile solutions of the disclosure may exert their neuroprotective effect through control of the p53 signaling pathway via p21.

Example 10

Antioxidant Property of Bile Solutions of the Disclosure

Cell viability was assessed by measurement of MTT reduction, which is an indicator of the pyridine nucleotide redox state of the cells. A human hybrid neuronal cell line ($1 \times 10^5$) (Neurobiology of Disease 11, 184-198, 2002) was seeded onto 96-well plates in 0.1 mL of medium and twenty-four hours later were exposed to the solution of Example 1. In addition, some cells were also exposed to hydrogen peroxide one hour after exposure to the bile solution (preincubation). Other cells were exposed to the bile solution at the same time as they were exposed to hydrogen peroxide. MTT assays were performed in accordance with Example 3.

Figure 12:
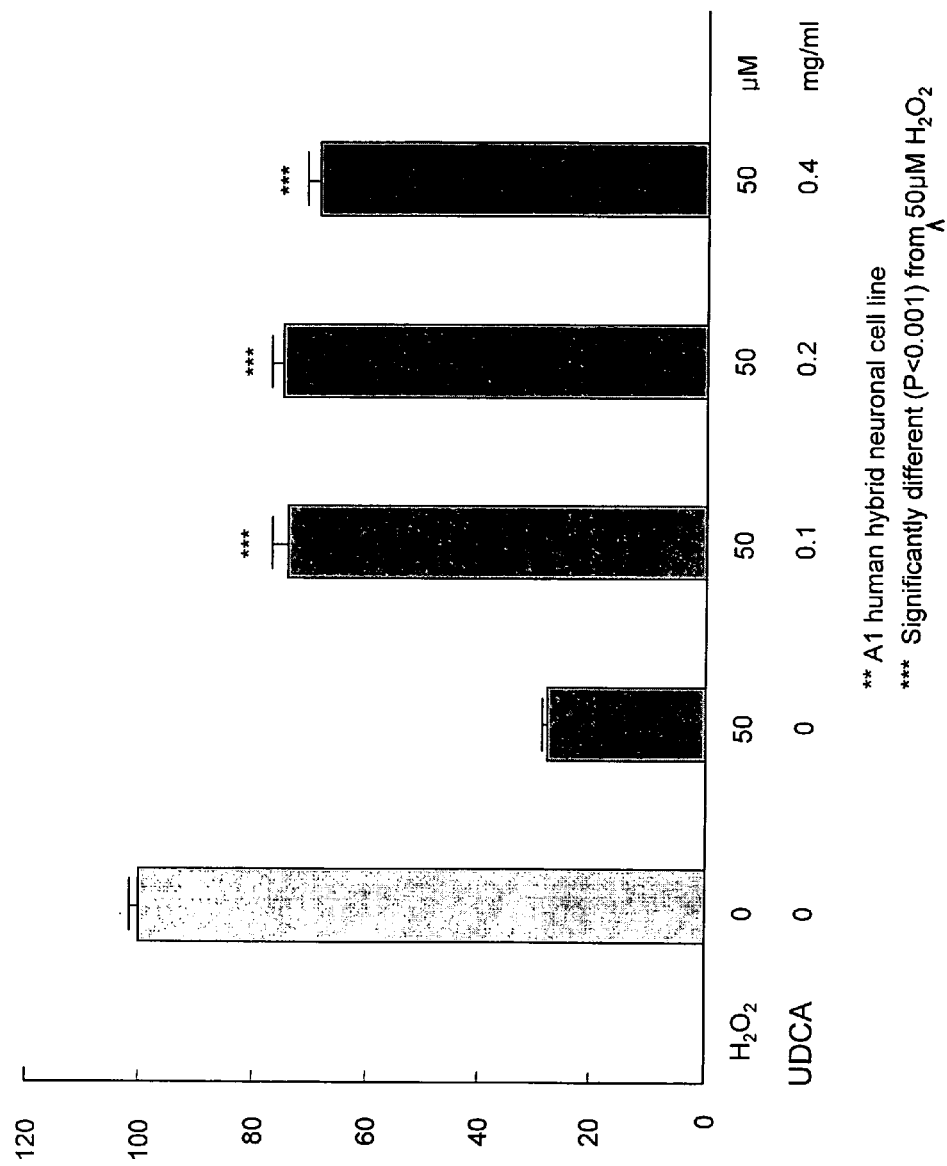
FIG. 12 is a bar graph showing the results of a cell viability assay in which A1 human hybrid neurons were incubated with 50 µM hydrogen peroxide and increasing concentrations of UDCA.

Results for pre-incubated cells, which were similar to simultaneously exposed cells, are shown in FIG. 12. Relative to the untreated control, exposure to hydrogen peroxide alone resulted in the death of about 75% of the cells. However, almost 80% of the hybrid neurons pre-treated with a UDCA solution of the disclosure survived treatment with hydrogen peroxide. Without limiting the present disclosure to any particular mechanism of action, these data suggest that solutions of the disclosure have antioxidant properties.

| APPENDIX |
| --- |
| Table of FIG. 1A |
| Treatment with Cisplatin for 48 hr |
| |
| CTL: 100 ± 11.2 (%, mean ± SEM) |
| Cisplatin 1 µM: 89.0 ± 9.7 |
| Cisplatin 5 µM: 67.3 ± 12.3 |
| Cisplatin 10 µM: 47.2 ± 8.4 |
| Cisplatin 20 µM: 39.0 ± 3.6 |
| Cisplatin 50 µM: 37.1 ± 5.7 |

-continued

APPENDIX

Table of FIG. 1B
Treatment with 20 μM cisplatin 0 hr: 100 ± 13.7
8 hr: 101.2 ± 15.3
12 hr: 96.7 ± 8.9
24 hr: 57.6 ± 9.2
36 hr: 42.3 ± 7.6
48 hr: 41.3 ± 4.3
Table 3 of FIG. 6A (n = 6)

Control = 100 ± 13.7%
Cisplatin 20 μM = 38.2 ± 4.6%
Cisplatin 20 μM + UDCA (0.1 mg/mL) = 41.3 ± 7.35%
Cisplatin 20 μM + UDCA (0.2 mg/mL) = 61.3 ± 8.67%
Cisplatin 20 μM + UDCA (0.5 mg/mL) = 79.2 ± 4.72%
Cisplatin 20 μM + UDCA (1.0 mg/mL) = 86.7 ± 6.84%
Cisplatin 20 μM + Vehicle = 35.2 ± 5.17%
Table 3 of FIG. 6B (n = 6)

Control = 100 ± 13.7%
UDCA (0.1 mg/mL) = 97.6 ± 15.7%
UDCA (0.2 mg/mL) = 104.3 ± 11.6%
UDCA (0.5 mg/mL) = 102.7 ± 4.8%
UDCA (1.0 mg/mL) = 95.3 ± 13.2%
Vehicle = 103.2 ± 9.7%
Table 4 of FIG. 10B for P53 (n = 3)

Control = 100 ± 21.3%
Cisplatin 20 μM = 383.5 ± 31.2%
Cisplatin 20 μM + UDCA (0.1 mg/mL) = 386.9 ± 13.5%
Cisplatin 20 μM + UDCA (0.2 mg/mL) = 339.0 ± 27.3%
Cisplatin 20 μM + UDCA (0.5 mg/mL) = 198.9 ± 19.7%
Cisplatin 20 μM + UDCA (1.0 mg/mL) = 175.1 ± 15.2%
Cisplatin 20 μM + Vehicle = 376.35 ± 22.6%
Table 4 of FIG. 10C for P21

Control = 100 ± 9.7%
Cisplatin 20 μM = 209.7 ± 11.8%
Cisplatin 20 μM + UDCA (0.1 mg/mL) = 202.2 ± 13.6%
Cisplatin 20 μM + UDCA (0.2 mg/mL) = 186.7 ± 10.3%
Cisplatin 20 μM + UDCA (0.5 mg/mL) = 122.3 ± 4.7%
Cisplatin 20 μM + UDCA (1.0 mg/mL) = 119.8 ± 8.8%
Cisplatin 20 μM + Vehicle = 200.15 ± 15.2%

\* p < 0.05
\*\* P < 0.01

What is claimed is:

1. A method of ameliorating or eliminating a p53-mediated toxic effect of a pharmaceutical compound in a subject comprising:
   administering to a subject a clear aqueous solution comprising:
   (a) a first material selected from the group consisting of a bile acid, a bile acid salt, and a bile acid conjugated with an amine by an amide linkage;
   (b) a carbohydrate selected from the group consisting of an aqueous soluble starch conversion product or an aqueous soluble non-starch polysaccharide;
   (c) water, wherein the first material and the carbohydrate both remain in solution for all pH values attainable in an aqueous solution; and
   administering a pharmaceutical compound that has a toxic effect in the subject, wherein the pharmaceutical compound is selected from the group consisting of cisplatin, carboplatin, oxaliplatin, suramin, bleomycin sulfate, mitomycin, epothitone, sulfasalazine, disulfiram, vincristine, vidarabine, leflunomide, and bortezomib.

2. A method according to claim 1, wherein the p53-mediated toxic effect is a neuropathic effect.

3. A method according to claim 1, wherein the p53-mediated toxic effect is axonal degeneration.

4. The method of claim 1, wherein the subject is a mammal.

5. The method of claim 1, wherein the subject is a human.

6. The method of claim 1, wherein the subject receives at least one dose of a pharmaceutical compound after said aqueous solution administration.

7. The method of claim 1, wherein said subject receives said pharmaceutical compound before said aqueous solution administration.

8. The method of claim 1, wherein said subject receives said pharmaceutical compound concurrently with said aqueous solution administration.

9. The method of claim 1, wherein the first material is selected from the group consisting of chenodeoxycholic acid, cholic acid, hyodeoxycholic acid, deoxycholie acid, 7-oxolithocholic acid, lithocholic acid, iododeoxycholic acid, iocholic acid, taurourodeoxycholic acid, taurochenodeoxycholic acid, taurodeoxycholic acid, glycoursodeoxycholie acid, taurocholic acid, glycocholic acid, their derivatives at a hydroxyl or carboxylic acid group on the steroid nucleus, their salts, or their conjugates with amines.

10. The method of claim 1, wherein the first material is ursodeoxycholic acid or a sodium salt of ursodeoxycholic acid.

11. The method of claim 1, wherein the selected pH range is between approximately 1 and approximately 10 inclusive.

12. The method of claim 1, wherein the aqueous soluble starch conversion product is selected from the group consisting of maltodextrin, dextrin, liquid glucose, corn syrup solid, and soluble starch.

13. The method of claim 12, wherein the aqueous soluble starch conversion product is maltodextrin.

14. The method of claim 1, wherein the aqueous soluble non-starch polysacceharide is selected from the group consisting of dextran, guar gum, pectin, indigestible soluble fiber.

15. The method of claim 1, wherein the pharmaceutical compound is selected from the group consisting of a chemotherapeutic compound, an antineoplastic compound, an immunoactive compound, a hydroxymethyl glutaryl coenzyme A reductase inhibitor, a proteosome inhibitor, an antiretroviral agent, and combinations thereof.

16. The method of claim 1, wherein the pharmaceutical compound is cisplatin.

17. A method of reducing or eliminating a p53-mediated neuropathic effect of a pharmaceutical compound in a human subject that receives a pharmaceutical compound, said method comprising:
   administering to the human subject the pharmaceutical compound that has a p53-mediated neuropathic effect, wherein the pharmaceutical compound is selected from the group consisting of cisplatin, carboplatin, oxaliplatin, suramin, bleomycin sulfate, mitomycin, epothitone, sulfasalazine, disulfiram, vincristine, vidarabine, leflunomide, and bortezomib,
   administering to the human subject a clear aqueous solution comprising:
   (a) a first material selected from the group consisting of a bile acid, a bile acid salt, and a bile acid conjugated with an amine by an amide linkage;
   (b) a carbohydrate selected from the group consisting of an aqueous soluble starch conversion product or an aqueous soluble non-starch polysaccharide; (c) water, wherein the first material and the carbohydrate both remain in solution for all pH values attainable in an aqueous solution.

18. The method of claim 17, wherein the pharmaceutical compound is selected from the group consisting of cisplatin, carboplatin, and oxaliplatin.

19. A clear aqueous solution comprising:
(a) a first material selected from the group consisting of an aqueous soluble bile acid, a bile acid salt, and a bile acid conjugated with an amine by an amide linkage;
(b) an aqueous soluble hydrolytic product of starch;
(c) a pharmaceutically effective amount of a chemotherapeutic compound selected from the group consisting of cisplatin and suramin; and
(d) water,
wherein the first material and the aqueous soluble hydrolytic product of starch both remain in solution at all pH values from about pH 1 to about pH 14.

20. The method of claim 1, wherein the pharmaceutical compound is selected from the group consisting of cisplatin, carboplatin, and oxaliplatin.

21. The method of claim 1 wherein the p53-mediated toxic effect of a pharmaceutical compound in a subject is manifest as a peripheral neuropathic effect.

22. A method of ameliorating or eliminating a toxic effect of a pharmaceutical composition comprising axonal degeneration in a subject comprising:
administering to a subject a clear aqueous solution comprising:
(a) a first material selected from the group consisting of a bile acid, a bile acid salt, and a bile acid conjugated with an amine by an amide linkage;
(b) a carbohydrate selected from the group consisting of an aqueous soluble starch conversion product or an aqueous soluble non-starch polysaccharide;
(c) water, wherein the first material and the carbohydrate both remain in solution for all pH values attainable in an aqueous solution; and
administering a pharmaceutical composition that has a toxic effect in the subject, wherein the pharmaceutical compound is selected from the group consisting of cisplatin, oxaliplatin, bleomycin sulfate, bortezomib, vincristine, isoniazid, vincaalkaloids, disulfram, sulfasalazine, and dapsone.

23. The method of claim 22 wherein the toxic effect of a pharmaceutical compound comprising axonal degeneration in a subject is manifest as a peripheral neuropathic effect.

24. The method of claim 22, wherein the axonal degeneration is p53-mediated.

* * * * *